(12) United States Patent
Kim et al.

(10) Patent No.: US 7,422,874 B2
(45) Date of Patent: Sep. 9, 2008

(54) EXPRESSION VECTOR FOR ANIMAL CELL

(75) Inventors: Jong-Mook Kim, Yongin-shi (KR);
Jung-Seob Kim, Suwon-shi (KR);
Sun-Mo Oh, Seoul (KR); Jae-Seung Yoon, Seoul (KR); Kwang-Hee Baek, Seoul (KR); Soo-Il Chung, Sungnam-shi (KR); Doo-Hong Park, Seoul (KR);
Yeup Yoon, Kwacheon-shi (KR)

(73) Assignees: Mogam Biotechnology Research Institute, Kyongi-do (KR); Neurotech Pharmaceuticals Co., Ltd., Gyeonggi-do (KR)

( * ) Notice: Subject to any disclaimer, the term of this patent is extended or adjusted under 35 U.S.C. 154(b) by 512 days.

(21) Appl. No.: 10/343,303

(22) PCT Filed: Jul. 27, 2001

(86) PCT No.: PCT/KR01/01285

§ 371 (c)(1),
(2), (4) Date: Aug. 4, 2003

(87) PCT Pub. No.: WO02/14525

PCT Pub. Date: Feb. 21, 2002

(65) Prior Publication Data

US 2004/0038394 A1    Feb. 26, 2004

(30) Foreign Application Priority Data

Jul. 29, 2000  (KR) .................. 10-2000-0043996

(51) Int. Cl.
*C12N 15/85* (2006.01)
*C12N 15/64* (2006.01)
*C12P 21/00* (2006.01)
(52) U.S. Cl. .................... 435/69.1; 536/23.1; 536/24.1
(58) Field of Classification Search .................. None
See application file for complete search history.

(56) References Cited

U.S. PATENT DOCUMENTS

| | | | | |
|---|---|---|---|---|
| 4,956,288 | A | * | 9/1990 | Barsoum ................... 435/6 |
| 5,108,901 | A | * | 4/1992 | Anderson et al. ............ 435/23 |
| 5,738,985 | A | * | 4/1998 | Miles et al. ................. 435/5 |
| 2003/0087342 | A1 | * | 5/2003 | Mermod et al. ............ 435/69.1 |

FOREIGN PATENT DOCUMENTS

| | | |
|---|---|---|
| EP | 0343783 | 11/1989 |
| KR | 2000009278 | 2/2000 |
| WO | WO94 07902 | 4/1994 |
| WO | WO97 27207 | 7/1997 |
| WO | WO97/46687 | 12/1997 |
| WO | WO97 47756 | 12/1997 |
| WO | 99/07866 | 2/1999 |

OTHER PUBLICATIONS

Walter et al., Biochem. Biophys. Res. Comm., 1998, vol. 242, pp. 419-422.*

Jinghua Yu, et al. A5 Beta-globin matrix-attachment region and the polyoma enhancer together confer position-independent transcription, vol. 139, No. 2; pp. 139-145; p. 142-p. 143, figure 1.

B. Gernardi et al., 1987, "A glimpse at chromosomal order" Trends in Genetics, 3, 16-22.

Kucherlapati et al., 1984, "Introduction of purified genes into mammalian cells" Crit. Rev. Biochem. 16, 349-379 (abstract only).

Palmiter et al., 1986, "Germ-line transformation of mice" Ann. Rev. Genet. 20, 465-499.

Eissenberg et al., 1991 "Boundary functions in the control of gene expression" Trends in Genetics, 7, 335-340.

Kalos et al., 1995, "Position-independent transgene expression mediated by boundary elements from the apolipoprotein B chromatin domain" Mol. Cell. Biol. 15, 198-207.

Klehr et al. 1991, "Scaffold-attached regions from the human interferon B domain can be used to enhance the stable expression of genes under the control of various promoters" BIOCHEMISTRY 30, 1264-1270.

Phi-Van, L. and Stratling, W.H, 1996 "Dissection of the ability of the chicken lysozyme gene 5' matrix attachment region to stimulate transgene expression and to dampen position effects" BIOCHEMISTRY 35, 10735-10742.

Kraevskii VA, et al. 1992 "Stably bent and low-melting DNA sequences at the origin of replication of chicken alpha-globulin gene domains" Mol. Biol. (MOSK) Sep.-Oct. 26 (5):1011-21 (abstract only).

Yu, J. et al. 1994 "A 5' B-globin matrix-attachment region and the polyoma enhancer together confer position-independent transcription" GENE 139(2), 139-145.

Kas, E., et al. 1987 Anchorage of the Chinese Hamster Dihydrofolate Reductase Gene to the Nuclear Scaffold Occurs in an Intragenic Region J. Mol. Biol. 198(4), 677-692.

Sykes, R.C., et al. 1988 "Yeast ARS function and nuclear matrix association coincide in a short sequence from the human HPRT locus" Mol. Gen. Genet. 212, 301-309.

Hanson, R.D., et al. 1992 "A-T -Rich scaffold attachment regions flank the hematopoietic serine protease genes clustered on chromosome 14Q11.2" BLOOD vol. 79, No. 3, 610-618.

Mielke, C. et al., 1990 "Hierarchical binding of DNA fragments derived from scaffold-attached regions: correlation of properties in vitro and function in vivo" BIOCHEMISTRY 29, 7475-7485.

(Continued)

*Primary Examiner*—David Guzo
(74) *Attorney, Agent, or Firm*—Fulbright & Jaworski

(57) ABSTRACT

The present invention relates to an expression vector for animal cells. Specifically, the present invention relates to an expression vector, pMS vector, pSG vector and pMSG vector, including the human β-globin 5' MAR complementary sequence or/and the transcription termination site of the gastrin gene. An expression system using an expression vector of the present invention can successfully produce recombinant proteins in various animals cells and recombinant protein having a unique structure and function.

5 Claims, 15 Drawing Sheets

OTHER PUBLICATIONS

Jagadeeswaran, P. et al., 1982 "A gene deletion ending at the midpoint of a repetitive DNA sequence in one for of hereditary persistence of fetal haemoglobin" NATURE 296, 469-470.

Rogers, John H., 1985, "The origin and evolution of retroposons" Int. Rev. Cytol. 93, 187-279.

Kaufman, Randal J. 1997 "Overview of Vector Design for Mammalian Gene Expression" Methods Mol. Biol. 62, 287-300.

Boulikas, T. 1993 "Homeodomain protein binding sites, inverted repeats, and nuclear matrix attachment regions along the human beta-globin gene complex" J. Cell. Biochem May;52(1):23-36.

Yan, Z. J. 1998 "The 5'-flanking cis-acting elements of the human epsilon-globin gene associates with the nuclear matrix and binds to the nuclear matrix proteins" Cell. Res Sep. 8(3):209-18.

Razin, Sergey V. et al 1999 "Functional analysis of DNA sequences located within a cluster of DNase I hypersensitive sites colocalizing with a MAR element at the upstream border of the chicken a-globin gene domain" J. Cell Biochem Jul. 1:74:38-49.

Van Drunen, Cornelis M. 1999 "A bipartite sequence element associated with matrix/scaffold attachment regions" Nucleic Acids Res Jul. 15;27(14):2924-30.

Theo D. Palmer et al., "Efficient Expression of a Protein Coding Gene under the Control of an RNA Polymerase I Promoter", Nucleic Acids Research, 1993, vol. 21, No. 15, pp. 3451-3457.

Kwang-Hee Baek et al., "RNA Polymearase II Transcription Terminates at a Specific DNA Sequence in a HeLa Cell-Free Reaction", Proc. Natl. Acad. Sci. USA, Oct. 1986, vol. 83., pp. 7623-7627.

Monica Lik-Shing Tsang et al., "Characterization of Recombinant Soluble Human Transforming Growth Factor-Beta Receptor Type II (rhTGF-Beta sRII)", Cytokine, Jul. 1995, vol. 7, No. 5, pp. 389-397.

Yodosha, "Experimental Medicine Independent Volume", Biomanual 4, Gene Transduction, Expression and Analysis, 1st edition, Japan (1994), pp. 133-141.

Kenzo Sato et al., "A Specific DNA Sequence Controls Termination of Transcription in the Gastrin Gene", Molecular and Cellular Biology, Apr. 1986, vol. 6, No. 4, (Apr. 1986), pp. 1032-1043.

European Patent Office Communication dated Jan. 15, 2007.

Japanese Office Action, Stamped Oct. 12, 2006.

English translation of Japanese Office Action.

* cited by examiner (β-glo-c : vector containing β-globin MAR,

β-glo -r : vector containing the β-globin MAR complement)

The positive cells transfected with control vector : ■

The positive cells transfected
with vector containing the β -globin MAR complement : □

EXPRESSION VECTOR FOR ANIMAL CELL

BACKGROUND OF THE INVENTION (a) Field of the Invention

The present invention relates to an expression vector for animal cells, and more particularly, to an expression vector including a nuclear matrix attachment region element (hereinafter referred to as "MAR element") and the transcription termination site of the gastrin gene.

(b) Description of the Related Art

Many kinds of expression systems, such as microorganisms, plants, yeasts, insect cells, and animal cells are currently in use for medical treatment through expression of the desired proteins in a large amount. Among the many kinds of expression systems, microorganisms are most easily used, and many kinds of microorganism systems are studied and utilized as expression systems.

However, the use of a microorganism expression system is limited in some respects. First, though genes are expressed, the structure and characteristics of an expressed protein are unlike that of an animal protein because a microorganism has a different mechanism for expressing proteins and for modifying protein by glycosylation, phosphorylation, and amidylation. Therefore, a recombinant protein produced by microorganisms has nearly no modification, and is limited to the production of proteins whose functions are not much affected by the differences in the modification and structure of the proteins. In addition, when the recombinant proteins expressed by microorganisms are used, a cleaning process for contamination by the microorganism or a toxin is needed.

Although animal cells are suitable for an animal's protein expression, an expression system using animal cells is not commonly used because the expression system using animal cells creates higher production costs due to a lower expression efficiency of recombinant protein compared to microorganisms.

Animal cells currently in use in industry as an expression system include. CHO (Chinese Hamster Ovary), BHK (Baby Hamster Kidney), and myeloma cells. An expression vector is introduced into an animal cell and a desired foreign protein is produced, similar to a microorganism.

Gene expression systems are modified by various methods, because generally a small amount of the foreign genes are expressed. For example, a cell strain of CHO cells is cultivated in medium containing methotrexate (hereinafter referred to as "MTX") which is an inhibitor of DHFR (Dihydrofolate reductase), in order to obtain a CHO strain which is alive, depending on MTX concentration, and highly expresses protein due to an increase in the copy number of genes.

Generally, when foreign genes are expressed in an animal cell, the foreign gene is co-transfected with a vector having a selective marker, and transformed cells are selected through cultivation in selective medium for many hours. However, the frequency of achieving a highly expressing cell clone is low. The low frequency of foreign gene expression is due to chromosomal insertion of the foreign gene in the animal system, unlike a microorganism. In addition, though the insertion process of the foreign gene is successful, the expression of the foreign gene cannot be expected since the inserted site of each gene differs and the expression of a gene depends on the inserted site (Grindley et al., 1987. Trends Genet. 3, 16–22; Kucherlapati et al., 1984. Crit. Rev. Biochem. 16, 349–381; Palmiter et al., 1986. Annu. Rev. Genet. 20, 465–499). Therefore, though foreign genes are stably integrated, they may be expressed in small amounts because most of the gene expression in animal cells is inhibited by the neighboring nucleic acid (Eissenberg et al., 1991. Trends Genet. 7,335–340; Palmiter et al., 1986. Annu Rev. Genet. 20, 465–499).

In order to protect the expression of the foreign gene from position effects, the possibility of using nuclear matrix elements in several systems has been reported. An exemplary nuclear element includes an insulator element, nuclear matrix attachment region (hereinafter referred to as "MAR"), and a scaffold attachment region (hereinafter referred to as "SAR").

Kalos (Kalos et al., 1995 Mol. Cell. Biol. 15, 198–207) suggested that when apolipoprotein B MAR combined with a minimal promoter transgene construct, the foreign gene was stably introduced in the host chromosome, so that the expressed amount of the transcript increased by about 200 times. Similar to the aforementioned method, it was reported that chicken lysozyme A MAR and β-interferon SAR are capable of increasing the expression level of a foreign gene in a vertebrate cell regardless of the chromosomal insertion site (Eissenberg et al., 1991. Trends Genet. 7, 335–340; Klehr et al, 1991. Biochemistry 30, 1264–1270). However, it has not been verified that the MAR and SAR are capable of increasing protein production in a CHO cell strain, or that the MAR and SAR are suitable for common use.

When an animal cell gene is expressed, mRNA synthesis occurs from the promoter and stops at the termination site. The levels of the expressed proteins are often influenced by the efficiency of transcription termination as well as the stability of the synthesized mRNA.

The transcriptional termination site which is included in an expression vector controls polyadenylation, and has an influence on mRNA stability. The termination site includes a poly-A signal, cleavage site, and termination site; the polyadenylation signal is AATAAA and is well studied. However, the cleavage site where polyadenylation occurs, and the termination site where the gene transcription is completed by RNA polymerase enzyme II are not well known. In addition, though it is reported that GU/U-rich region except the three kinds of critical region controls the polyadenylation of mRNA, the detailed mechanism is not known.

Expression vectors which are commonly used in animal cells contain a poly-A signal of SV40 virus and BGH (Bovine Growth Hormone). It has not been suggested that a specific terminator that improves mRNA stability and the expression level be developed in order to use an expression vector in animal cells.

SUMMARY OF THE INVENTION

It is an object of the present invention to provide an expression vector having increased expression efficiency and levels for foreign genes in the expression of foreign proteins used in an animal cell system.

In order to achieve these objects, this invention provides an expression vector comprising a MAR (Nuclear Matrix Attachment Region) element or its complementary sequence at the 5'-terminal end of a promoter.

Also, this invention provides an expression vector for animal cells comprising a construct consisting of an SV 40 virus poly-A (polyadenylation) signal and the transcription termination site of the gastrin gene, wherein the construct has the sequence of SEQ ID No. 3.

Also, this invention provides a pMSG KCCM 10202 vector of SEQ ID No. 8, comprising a complementary sequence of the human β-globin 5' MAR (nuclear matrix attachment region), and the construct consisting of the SV 40 virus poly-A signal and the transcription termination site of the gastrin gene.

Also, this invention provides a preparation method for bioactive materials by using an expression vector for animal cells comprising a β-globin MAR element, or the β-globin MAR complementary sequence at the end of promoter 5'-terminal, and a vector comprising the SV40 virus poly-A (polyadenylation) signal of SEQ ID No. 3 and the transcription termination site of the gastrin gene, and a pMSG vector.

DETAILED DESCRIPTION OF THE-PRESENT INVENTION

Hereinafter, the present invention will be explained in detail.

The inventors overcame problems arising from the site-specific effect when foreign genes are expressed in animal cell systems, and designed an optimal expression vector that increases the expressed amount of the genes.

An expression vector for animal cells of the present invention comprises suitable base sequences, which are further added to conventional expression vectors. The suitable base sequences include a nuclear matrix attachment region (hereinafter referred to as "MAR") and a scaffold attachment region (hereinafter referred to as "SAR"), which stimulate foreign gene expression in a host such as CHO (Chinese hamster ovary) and BHK (baby hamster kidney) cells from position effects at the insertion site, and increase the expressed amount of the foreign genes.

The MAR or SAR element is added to the 5'-terminal end of a promoter and the efficiency of the expression vector of the present invention is analyzed. Chromosomal DNA is isolated from the cell, and cloned in *E. coli* through PCR (polymerase chain reaction) and sub-cloning, so that the DNA of the MAR and SAR elements is obtained.

Preferably, the MAR or SAR element is selected from the group consisting of chicken lysozyme 5' MAR (Phi-Van, L. and Stratling, W. H., Biochemistry 35, 10735–10742 (1996), gene bank #: X98408), chicken pi α globin 5' MAR (Krevskii, V. A., Mikhailov, V. S. and Razin, S. V., Mol. Biol. 26, 672–678 (1992), gene bank #: X64113), a human β-globin 5'MAR (Yu, J., Bock, J. H., Slightom, J. L. and Villeponteau, B., Gene 139(2), 139–145 (1994), gene bank #: L22754), CHO DHFR intron MAR (Kas, E. and Chasin, L. A., J. Mol. Biol. 198(4), 677–692 (1987), gene bank #: X06654), a human HPRT intron MAR (Sykes, R. C., Lin, D., Hwang, S. J., Framson, P. E. and Chinault, A. C., Mol. Gen. Genet. 212. 301–309 (1988), gene bank #: X07690), a human CSP-B gene flanking SAR (Handson, R. D. and Ley, T. J., gene bank #: M62716), and a human interferon β-gene flanking SAR (Mielke, C., Kohwi, Y., Kohwi-Shigematsu, T. and Gode, J., Biochemistry 29, 7475–7485 (1990), gene bank #: M83137).

The MAR and SAR elements were integrated in an expression vector for animal cells, and β-Gal expression of the vector was induced in order to confirm the relation between the MAR/SAR elements and the expression titer.

Figure 1:
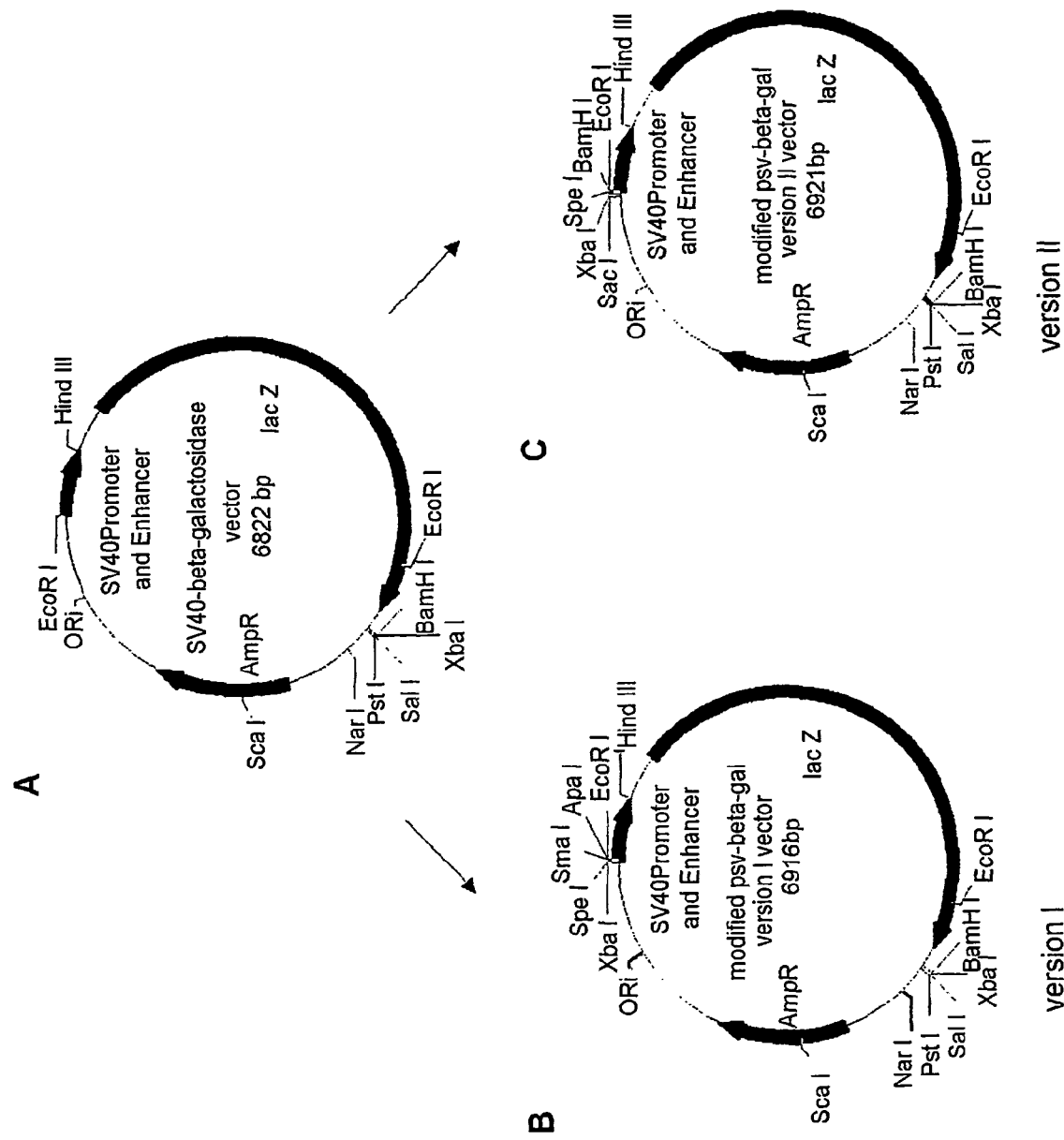
FIG. 1 (Parts A–C) shows a structure of an expression vector, which is prepared by combining an SV40 promoter and the β-gal gene for reporter of gene expression.

The 5'-terminal end of the pSV-β-gal promoter was connected to a multicloning site (hereinafter referred to as "MCS") by in vitro PCR mutagenesis and then a recombination vector (version I and version II vector) was obtained, as shown in FIG. 1. The MAR or SAR was inserted in front of the 5'-terminal end of the SV40 promoter of the recombination vector pSV-β-gal version I or II, a test vector was prepared, and the test vector were transformed into CHO DG44 cells. The transformed CHO DG 44 cells were selected on media containing G418 (neomycine), and the expression titer was measured by staining β-Gal (blue staining with IPTG and X-Gal). To measure the expression titer, the expression frequency, the number of the expression cells, and the amount of β-Gal expression were measured.

Figure 2:
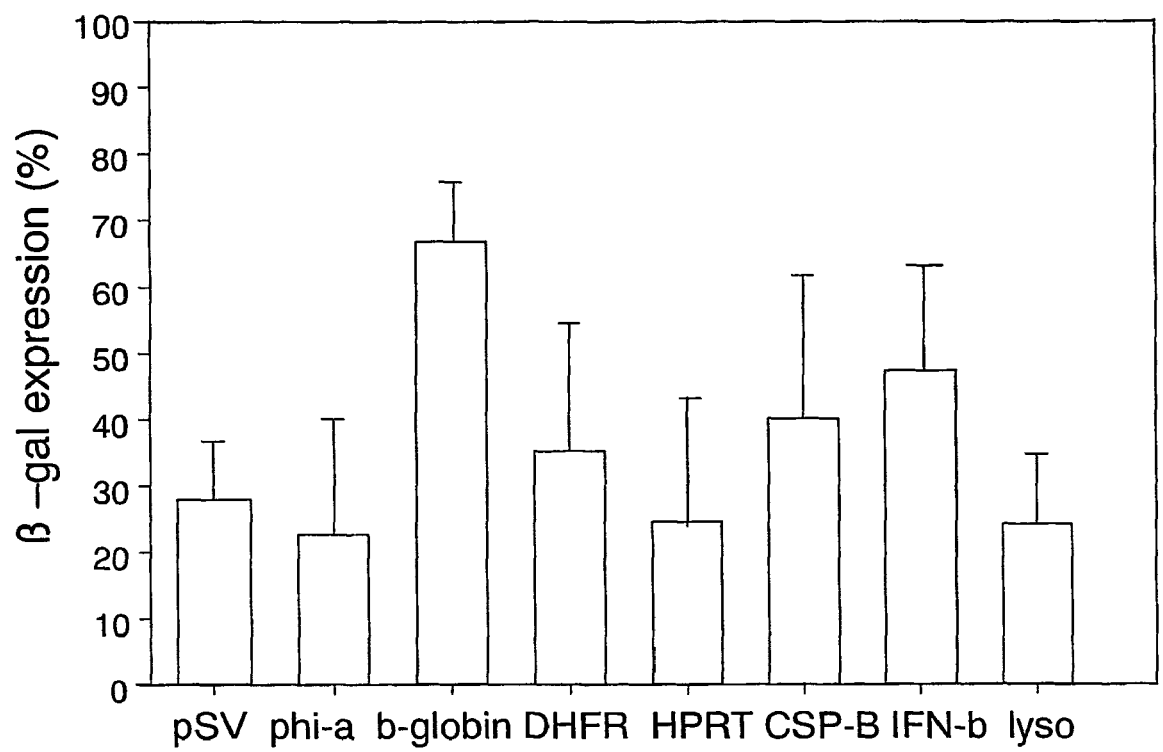
FIG. 2 shows an expression frequency of β-Gal induced by various MAR and SAR elements that are used in the present invention.

FIG. 2 shows the expression frequency of β-Gal induced by various MAR and SAR elements used in the present invention. The pSV-β-gal vector showed about 20 to 30% of β-Gal expression frequency, whereas the test vector comprising β-globin MAR, CSP-B SAR or interferon β SAR increased the expression frequency in positive cell lines, and more particularly, the test vector comprising β-globin MAR showed about 70 to 80% of β-Gal expression frequency.

In addition, constructs were prepared according to a combination of various MAR elements and the SV40 promoter, and the influence of recombinant protein expression was compared to SV40 virus promoter. In order to compare the amount of β-Gal production, a β-Gal staining method and a measurement method of β-Gal enzyme were operated. The activity of β-Gal was analyzed in the same number of positive cell lines, since the expression frequency differs according to each MAR element.

Figure 3:
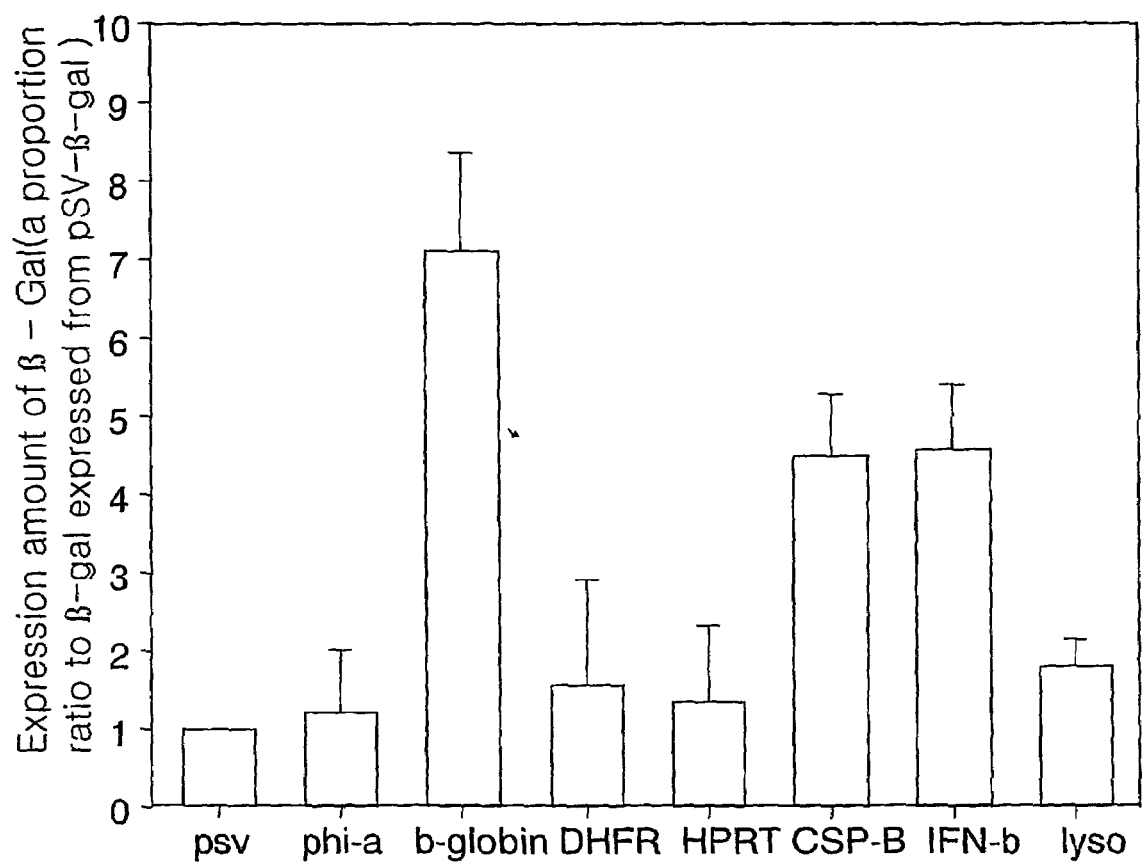
FIG. 3 shows the activity of expressed β-Gal, which indicates an influence on β-Gal expression by the MAR and SAR elements of the present invention.

FIG. 3 shows the activity of expressed β-Gal according to the influence of various MAR and SAR elements. The β-Gal amount per positive cell or the activity of β-Gal increased, when the β-globin MAR, CSP-B SAR, and interferon β-SAR elements were used, compared to pSV-β-gal. It is observed that the expression amount of the vector comprising the β-globin MAR element increased by 7 times or more.

Accordingly, among MAR elements, the β-globin MAR element is preferable.

The DNA sequence of the MAR element was analyzed in order to investigate the effect and efficiency of the β-globin MAR element.

The β-globin MAR element includes 2,999 bases and their function is not found in detail. The β-globin MAR element comprises a consensus sequence and a 244 bp alu element which is located 3' of an 800 bp region and where A+T (Adenine, Thymidine) rich sequences exist. It is reported that the alu site comprises 300 bp of two directly repeating monomer units, and recombination often occurs at this site, since thousands of homologous sites exist in a chromosome of an eukaryote (Jagadeeswaran et al., 1982. Nature 296, 469–470; Rogers. 1985. Int. Rev. Cytol. 93, 187–279). When the alu of β-globin MAR exists upstream of the SV 40 promoter, and the cell is cultivated for a long time, recombination can occur.

Therefore, the inventors designed β-globin MAR mutants that do not have the aforementioned negative effect.

Figure 4:
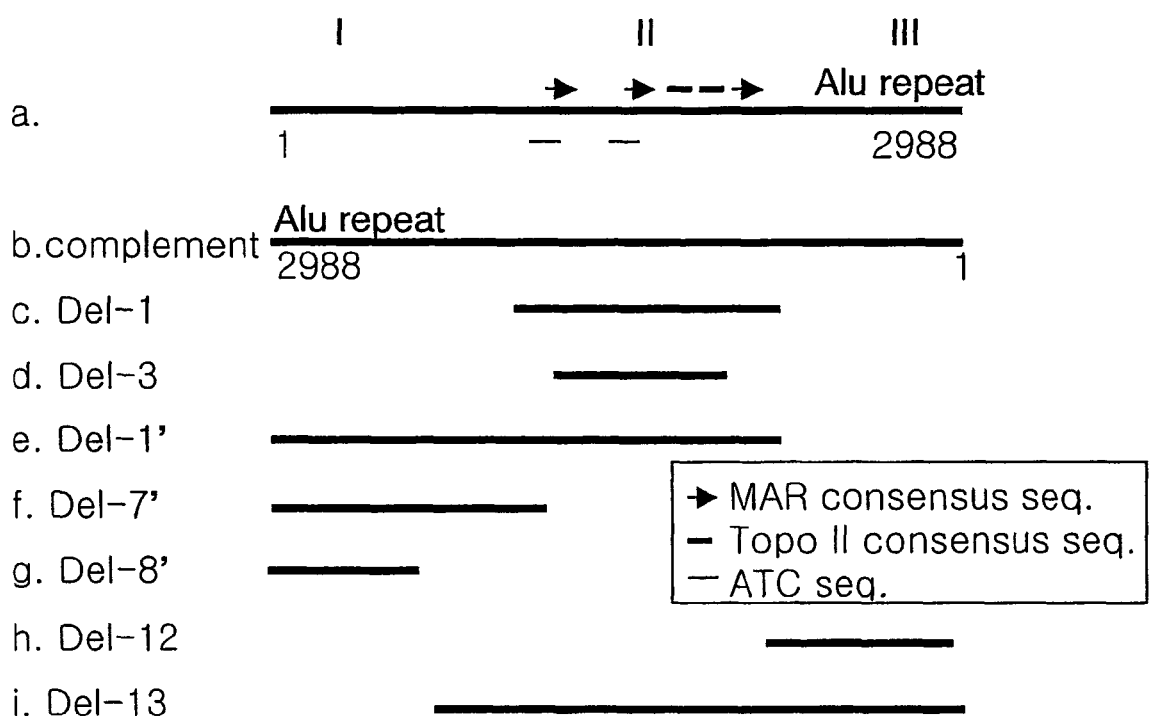
FIG. 4 shows various mutant constructs of the MAR element based on the β-globin MAR DNA sequence of the present invention.

FIG. 4 shows the β-globin MAR mutants, which are produced by preparing the MAR complementary sequence b, deletion mutant c, d, e, f, g and i, and integrating them into the pSV-β-gal version I.

Figure 5:
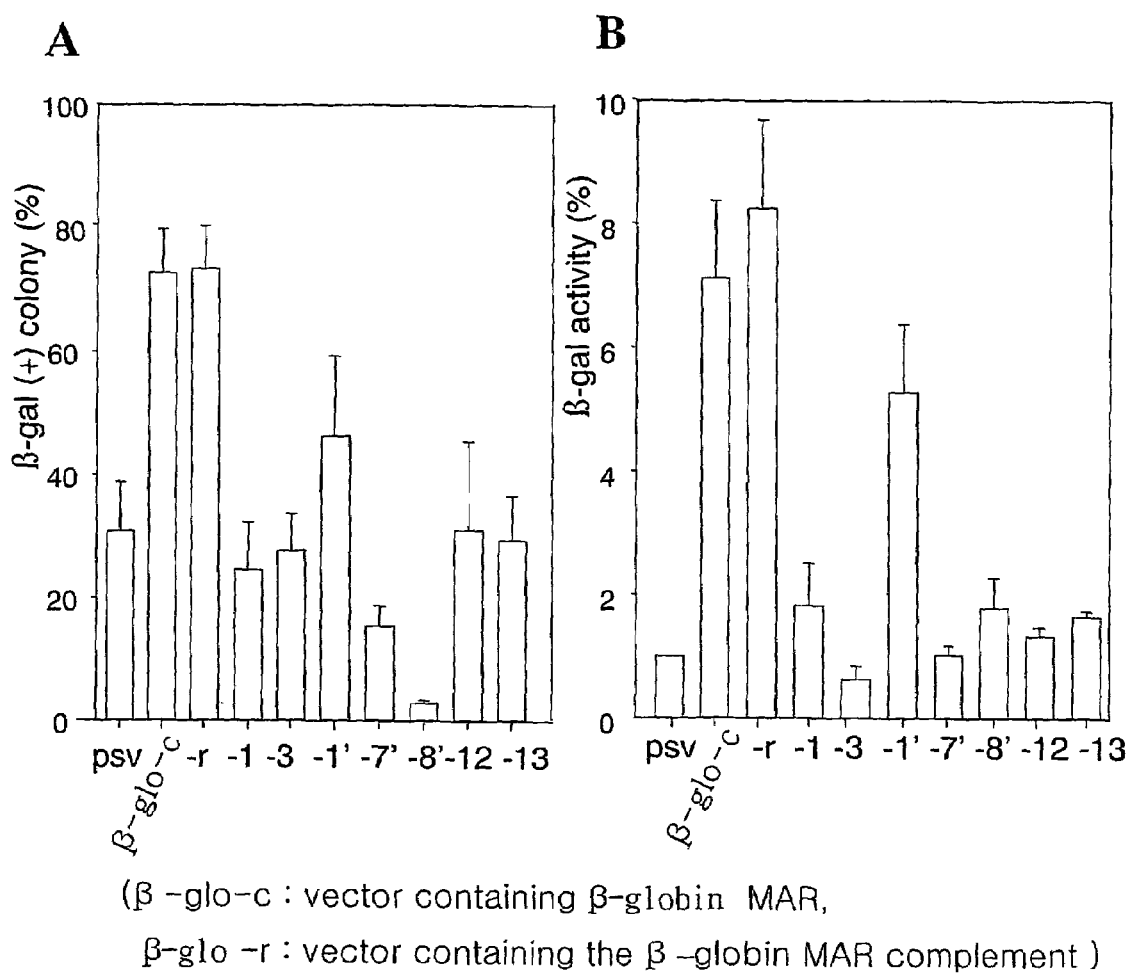
FIG. 5 (Parts A–B) shows the expression frequency and expression amount of β-Gal proteins, after the transfection of a vector with MAR elements into CHO cells.
Figure 6:
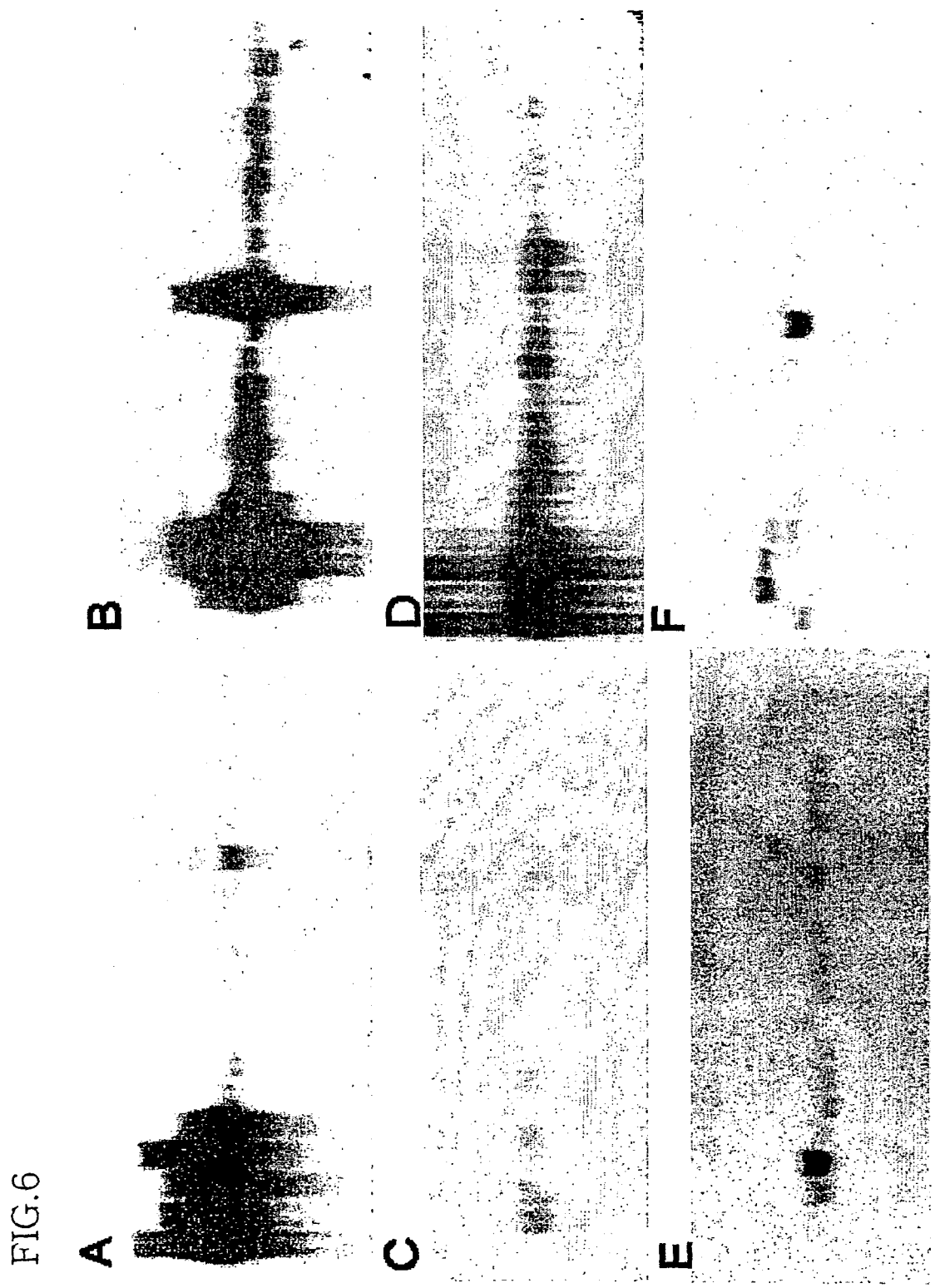
FIG. 6 shows the Southern and Northern blots confirming β-Gal gene copy number (a: a control group, b: the present invention), RNA number (c: a control group, d: the present invention), and copy number of the neo gene as a selective marker (e: a control group, f: the present invention) in animal cells transformed with pMS-β-gal or pSV-β-gal vector as the control.
Figure 7:
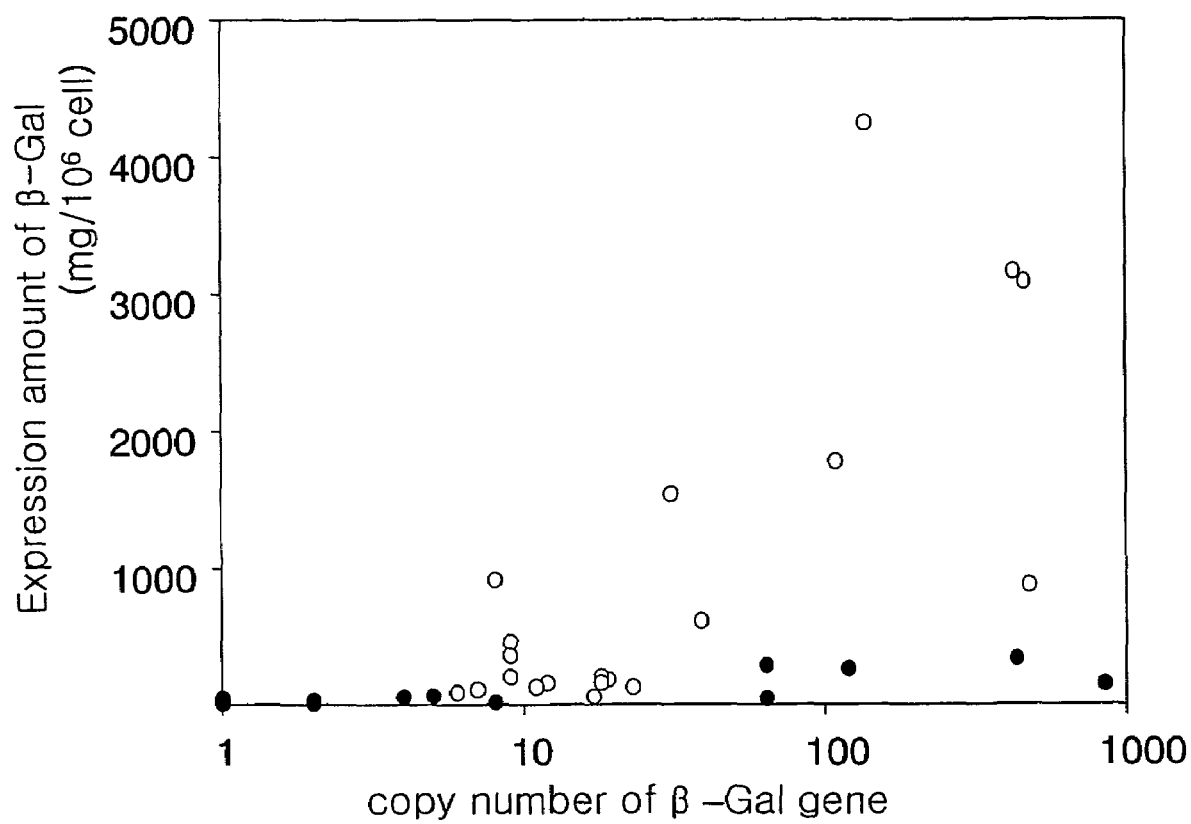
FIG. 7 is a graph showing the relationship between the copy number of the β-Gal gene and the expression yield of β-Gal in animal cells transformed with the pMS-β-gal or with pSV-β-gal vector as the control group.

After the vector comprising the β-globin MAR mutant was introduced into CHO cells, the cell number of β-Gal expression and the amount of 1-Gal were measured. The results are represented in FIG. 5. The β-Gal expression titer of most of the β-globin MAR mutants decreased; in contrast, that of the cell line transformed with pMS-β-gal vector comprising a β-globin MAR complementary sequence was high. FIGS. 6 and 7 show the relation between the expressed amount of recombinant protein and the copy number of the integrated genes. The expressed amount of pSV-β-Gal is independent of the copy number of the integrated genes, and the expressed amount of the transformed vector with pMS-β-Gal is proportional to the copy number of the integrated genes. Since the β-globin MAR complementary sequence allows alu to exist on the other side of the promoter, the possibility of recombination of the vector decreases, and the expressed amount increases by the prevention of the insertion site specific effect. Therefore, the β-globin MAR complementary sequence is preferable in the present invention.

It is verified that the MAR or SAR element is located at the 5' site of the conventional expression vector's promoter, and that the MAR or SAR mutants, or complementary sequence are integrated into the conventional expression vector, so that the expression titer of the foreign proteins increase. Therefore, the present invention provides an expression vector including a MAR or SAR element, and expression vectors including MAR or SAR mutants, or their complementary sequence. The MAR or SAR element is preferably selected from the group consisting of pi-a MAR (chicken pi α-globin 5'MAR), β-globin MAR (human β-globin 5' MAR), DHFR MAR (CHO DHFR intron MAR), HPRT MAR (human HPRT intron MAR), CSP-B SAR (human CSP-B gene flanking SAR element), interferon-β SAR element (human interferon-β gene flanking SAR element), and lyso MAR (chicken lysozyme 5' MAR).

Among them, the pMS vector (KCCM-10203) of the present invention consisted of 6287 bp comprising the human β-globin MAR complementary sequence at the 5' terminal end of a SV 40 virus promoter and multicloning sites, and is capable of expressing a recombinant protein by the integration of genes into the multicloning sites. The pMS base sequence is compiled as SEQ ID No. 1 with Sequence Listing software.

When the β-globin MAR complementary sequence is used, the expression frequency and the expressed amount of the foreign genes increase by 3 to 4 times, and by 7 to 10 times, respectively, compared to foreign genes when only the SV40 promoter is used. In addition, the pMS-β-gal vector is applicable to the various kinds of animal cells, represented in FIG. 8, and the pMS-β-gal vector system is preferably applicable to BHK, CHO, NIH3T3, and HEK 293 cells. FIG. 9 shows expression titer increments by adding MTX (methotrexate) when foreign proteins are expressed in the pMS-β-gal vector system.

To measure the expression titer of foreign proteins according to MAR or SAR, CMV (cytomegalo virus) promoter is used. Since the expression titer of foreign genes differs depending on the kind of promoter and cell strains, the CMV promoter is also tested. In order to verify the effect of the β-globin MAR complementary sequence on the function of the CMV promoter, pMC vector is prepared by a procedure similar to pMS preparation, and scu-PA genes are integrated into pMS, pMC, and the control vector.

Figure 10:
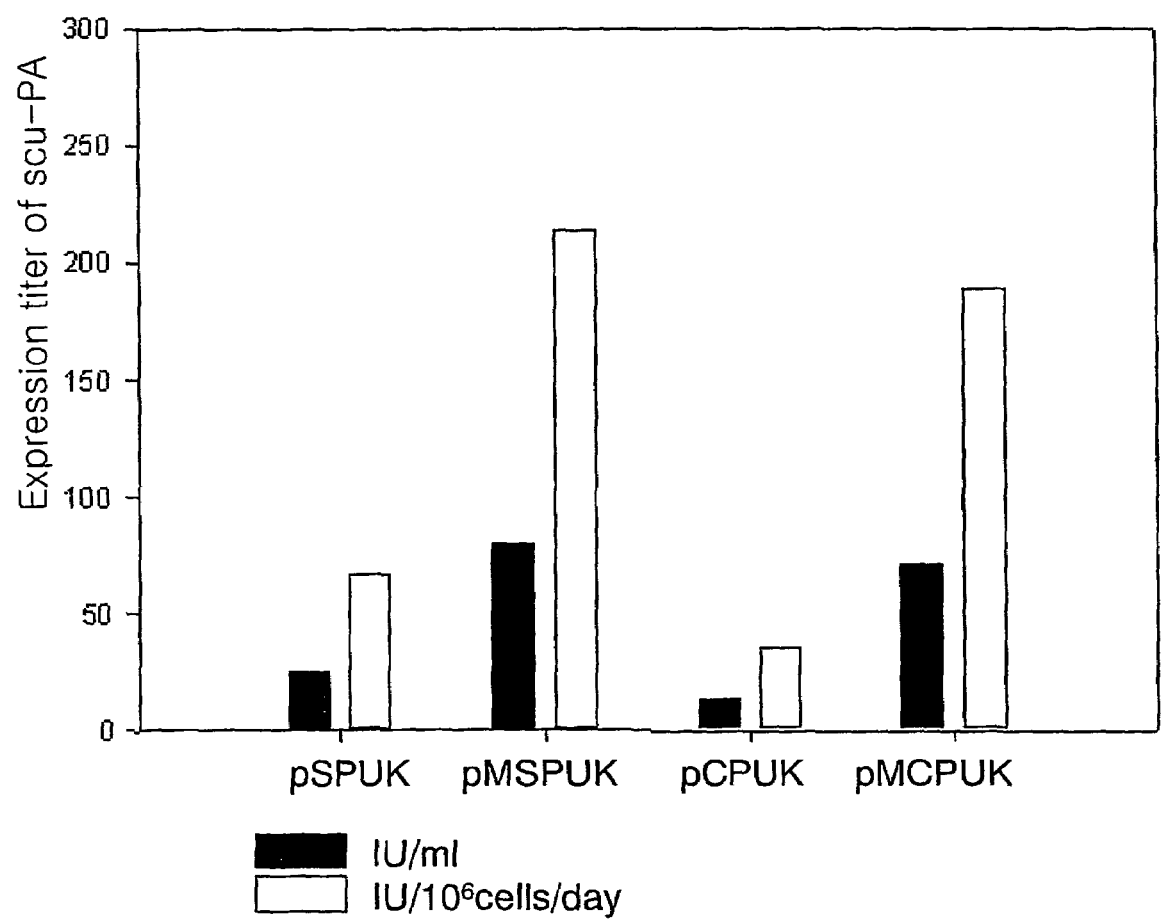
FIG. 10 shows the expression titer of scu-PA, after the scu-PA (single chain prourokinase) was inserted into the pMS vector and the pMC vector, compared to that of the control.

FIG. 10 shows the expression titer of scu-PA in CHO transformed with pMSPUK, pMCPUK, pSPUK, and pMCPUK vectors which are prepared by integrating the scu-PA into pMS, pMC, pSV, and pCMV. Gene expression of pMS and pMC increased by 4 times that of pSV and pCMV. Therefore, the β-globin MAR complementary sequence of the present invention can be used for protein expression of animal cells by suitable combination with the desired promoters.

Since the vector of the present invention including the β-globin MAR complementary sequence is integrated with foreign genes as the host cell, useful proteins can be obtained from an animal cell strain in the conventional method.

In the present invention a human gastrin gene transcription poly-A signal, a cleavage site and a human gastrin termination site were prepared, and were applied to the expression vector of the present invention in order to increase mRNA stability, thereby increasing the efficiency of the expression vector.

The human gastrin gene, 3' transcriptional regulatory region comprises 605 bp including a poly-A signal, cleavage sites, and a termination site. The base sequence of the human gastrin gene, 3' transcriptional regulatory region is filed as SEQ ID No. 2. The cleavage site is located 15 bp downstream from the poly-A signal, and the termination site is located 220 bp downstream from the poly-A signal. The transcription of gastrin is completed at the termination site and cleavage and polyadenylation of mRNA occur at the cleavage site.

Figure 11:
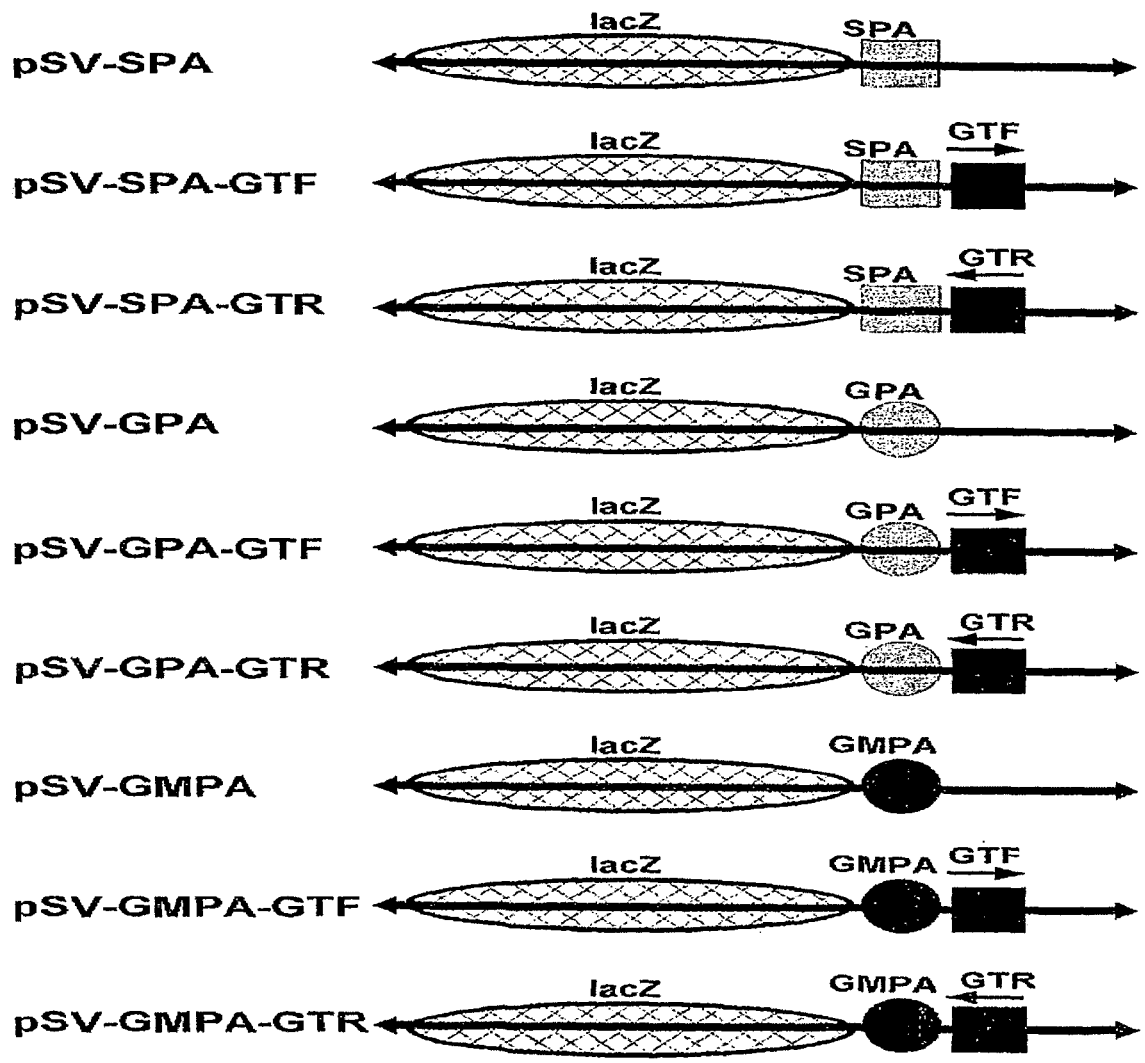
FIG. 11 shows a construct including the transcription termination site of the gastrin gene and the SV40 poly-A signal.

The construct consisting of SV 40 poly-A and the transcription termination site of the gastrin gene, which is capable of increasing the expression titer of genes, is shown in FIG. 11.

FIG. 11 shows constructs consisting of the transcription termination site of the gastrin gene and SV 40 poly-A. The constructs are preferably selected from pSV-SPA (SPA; the signal of SV 40 polyadenylation) in "a", pSV-SPA-GTF (GTF; transcription termination site of the gastrin gene) in "b", pSV-SPA-GTR (GTR; GTF complementary sequence) in "c", pSV-GPA (GPA; gastrin polyadenylation signal) in "d", pSV-GPA-GTF in "e", pSV-GPA-GTR in "f", pSV-GMPA (GMPA; GPA mutant) in "g", pSV-GMPA-GTF in "h", pSV-GMPA-GTR in "i". The base sequences of the SPA-GTF, SPA-GTR, SPA-GPA, SPA-GPMA are listed as SEQ ID No. 3, No.4, No. 5, and No.6, respectively. All the constructs were respectively integrated into pSV-β-gal, and further introduced to a COS-7 cell strain in order to measure the expression titer of β-Gal. The expression titer is the expressed amount of β-Gal, represented in FIG. 12. The pSG vector comprising the construct consisting of SV 40 poly-A signal and the transcription termination site of the gastrin gene has an effect in increasing the expressed amount of the protein 4 times. Therefore, the termination site is preferably SPA-GTF (the SV 40 poly-A signal and the transcription termination site of the gastrin gene) to increase the expression titer. In the present invention, the constructs are used as the termination site of the conventional expression vectors, so that the expressed amount of the foreign proteins increases. The exemplary expression vector of the present invention includes pSG.

The pSG vector is an integrated vector with SPA-GTF at its termination site, and 3309 bp. The base sequence of the pSG vector is listed as SEQ ID No. 7. The pSG vector was inserted with β-Gal in order to measure expression titer, and the expression titer of the pSG is 4 times larger than that of the pSV vector, which results from stabilizing mRNA by a construct consisting of the transcription termination site of the gastrin gene and the SV 40 virus poly-A signal.

Therefore, the vector comprising SPA-GRF can express foreign genes in an animal host in a conventional manner, and useful proteins such as a bioactive material can be obtained.

In addition, the present invention provides an expression vector including two sites that are capable of increasing the expression titer of foreign genes. The two sites are the transcriptional termination site linking the transcription termination site of the gastrin gene with the SV 40 poly-A, and the β-globin MAR complementary sequence.

Figure 13:
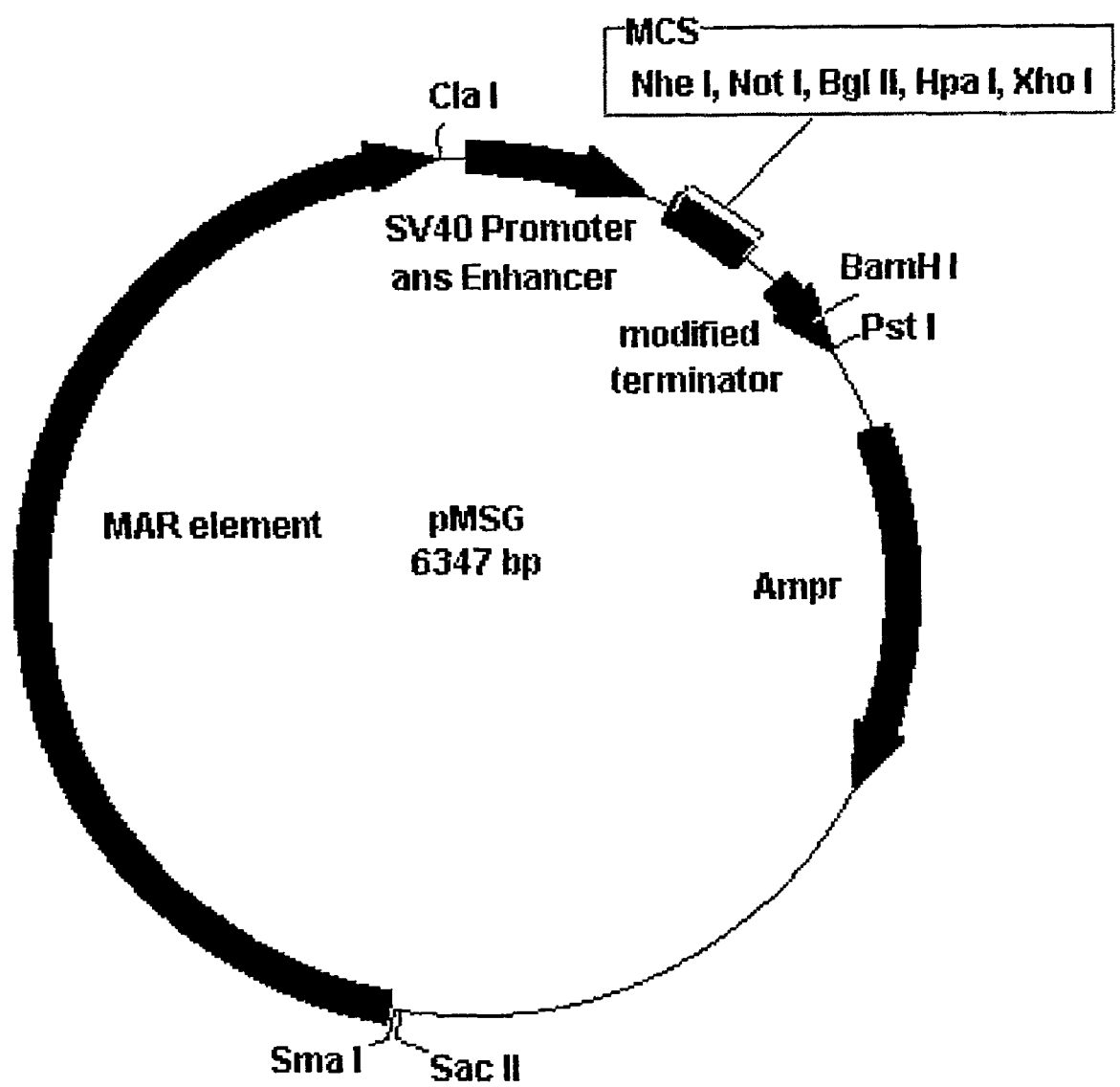
FIG. 13 shows the pMSG structure of the present invention.

FIG. 13 shows the pMSG structure of the present invention; 6347 bp of total base sequences are listed as the SEQ ID No. 8. pMSG was deposited under KCCM 10202 in Korea Culture Center of Microorganisms. The following Table 1 shows the map of pMSG in detail.

TABLE 1

| SEQ ID No. | Function |
| --- | --- |
| 1–419 | The early promoter of SV 40 and enhancer |
| 420–448 | Multicloning sites (MCS) |
| 449–656 | Transcriptional termination site |
| 3365–6329 | β-globin MAR complementary sequence |
| 1272–2132 | β-lactamase (AmpR) |

The protein for the TGF-β SRII gene is capable of preventing the side effects of TGF-β by selectively-binding with TGF-β. TGF-β SRII was expressed in order to analyze the effect and efficiency of pMSG of the present invention. As a result, in FIG. 14, since the TGF-β SRII protein has a glycosylation structure, the protein has a greater molecular weight than that of the original protein, as is typical of animal cells. The initial expressed amount of TGF-β SRII is about 100 ng/$10^6$ cells/day, and most of the cells are equally expressed. In addition, as shown in FIG. 15, 10 μg/$10^6$ cells/day were obtained at most, when 1 μM of MTX was added to the TGF-β SRII cells. TGF-β has various functions in the human body. In particular, it is found as a factor resulting in inflammation such as in corpora glomerulus sclerosis of the kidney, hepatic cirrhosis, cornification of epidermal cells, and occlusal cartilage. TGF-β SRII can be used for treatment of TGF-β-overexpressed disease.

The pMSG vector of the present invention has overcome a general problem, that is low expression yield and difficulty of obtaining transformants, and is capable of mass production of various kinds of recombinant proteins such as bioactive materials.

In addition, the pMS vector (KCCM-10203) was developed, which is not inhibited in its expression by neighboring bases at the insertion site, and pMS produced recombinant protein by about 8 times more than the conventional SV 40 promoter.

Also, the pSG vector was prepared, which comprises a transcriptional termination site that is capable of the induction of transcriptional termination at a specific site of a transcript and increasing by 3 times that of the conventional poly-A site.

The pMSG vector (KCCM-10202) of the present invention is prepared by connection of the functional DNA fragments and a multi-cloning site which is applicable to foreign genes. The expressed amount of it is 10 μg/$10^6$ cells/day, when TGF-β is expressed in animal cells. Accordingly, the expression vector of the present invention is suitable for the expression of recombinant proteins, and according to the present invention, a protein derived from a eukaryote can be produced in animal cells as a recombinant protein having the same structure and function compared to wild type protein.

The following Examples further illustrate the present invention in detail but are not to be construed to limit the scope thereof.

EXAMPLE 1

The Preparation of pMS-β-gal Vector (1) Preparation of pMS-β-gal Vector
A pMS-β-gal vector was prepared as follows.
① Genomic DNA Isolation from a G-2 Cell in Order to Obtain a Base Sequence of Human 3-globin MAR A genomic DNA is isolated from a G-2 cell in a human host by use of a Wizard Genomic DNA purification kit (a product of Promega Co.), and the purification procedure followed the experimental procedure supplied by the production company.
② Perform Genomic PCR and Subcloning In order to obtain a fragment of human β-globin 5' MAR, the purified genomic DNA was used as a template, and a sense primer BML1 and antisense primer BMR 1 for β-globin MAR were used in genomic polymerase chain reaction (PCR). BML1 and BMR1 were listed as a SEQ ID No. 9 and a SEQ ID No. 10, respectively. The PCR was performed with 32 cycles. Table 2 shows the cycle numbers.

TABLE 2

| | Experimental condition | Cycle numbers |
| --- | --- | --- |
| 1 | 94° C., 2 min. | 1 |
| 2 | 94° C., 30 sec. → 60° C., 45 sec. → 72° C., 45 sec. | 2–31 |
| 3 | 72° C., 10 min. | 32 |

After the PCR, the PCR product was inserted into the pT7blue vector (Novagen Co.), and the pT7blue/β-globin MAR vector was prepared. The pT7blue vector is a TA cloning vector which is capable of cloning a PCR product directly.

(3) Preparation of Recombinant Vector pSV-β-gal Version I and Version II Containing Multicloning Site (MCS)

In order to insert β-globin MAR of the pT7blue vector at the upstream of the promoter of the pSV-β-gal vector, the pSV-β-gal version I and the pSV-β-gal version II were prepared.

First, in order to prepare the pSV-β-gal version I, after the pSV-β-gal was treated with Spe I and Hind III, a 443 bp Spe I/Hind III fragment including the SV 40 promoter was purified from an agarose gel with a gene clean III kit (BIO 101 Co.). The fragment was ligated to linearized pBluescript SK(+) (Stratagene Co.) by Spe I/Hind III digestion, and pBluescript/SV40 I promoter vector was prepared.

Then, the pBluescript/SV 40 I promoter vector was treated with Sca I and Hind III, a fragment including the SV 40 promoter was purified from an agarose gel as in the same manner of the aforementioned, and the fragment was ligated with linearized pSV-β-gal vector Sca I and Hind III digestion, so that the version I vector was prepared.

In addition, in order to produce the pSV-β-gal version II vector, after the pSV-β-gal was treated with EcoR I and Hind III, and the 420 bp EcoR I/Hind III fragment including the SV 40 promoter was purified from an agarose gel as in the same manner of the aforementioned, the fragment was ligated with linearized pBluescript SK(+) by EcoR I and Hind III digestion, so that the pBluescript/SV 40 II promoter vector was produced.

The pBluescript/SV 40 II promoter vector was treated with Sca I and Hind III in order to purify a fragment including the SV 40 promoter from an agarose gel as in the same manner of the aforementioned, and the fragment was ligated with the linearized pSV-β-gal vector by Sce I and Hind III digestion, so that the pSV-p-gal version II vector was prepared.

(4) Preparation of a pMS-β-gal Vector

The pT7blue/β-globin MAR vector was treated with Spe I and Sma I and a DNA fragment in the size of 3 kb including the β-globin MAR was purified from an agarose gel. The fragment was ligated with linearized recombinant pSV-β-gal version I by Spe I and Sma I, so that β-globin MAR was cloned. In order to confirm the orientation of β-globin MAR, restriction enzyme Hind III confirmed that the β-globin MAR was cloned in reverse orientation to the pSV-β-gal version I vector.

(2) Expression Titer of the pMS-β-gal Vector

2 μg of the test vectors including the pMS-β-gal vector were co-transfected into CHO DG44 with pSV2neo vector using DOSPER (a product by Roche), and the pSV-β-gal vector as control vector was co-transfected in the same manner. The transfected CHO DG44 cells were cultivated in a selective medium that was MEM-α medium including nucleosides supplemented 10% heat-inactivated FBS and 850 μg/ml G418 sulfate (a product by Calbiochem Co.). Stably-transfected G418-resistant transfectants were generated after about 2 weeks, and twenty stable clones expressing β-Gal for control vector and pMS-β-gal vector in G418-resistant transfectants were isolated. 40 positive clones were analyzed by Southern and Northern blotting in order to measure the copy number of the β-Gal gene and the neo gene and the amount of the β-Gal RNA which is transcribed from pSV-β-gal and the pMS-β-gal.

FIG. 6 shows Southern and Northern blots confirming β-Gal gene copy number (a: a control group, b: the present invention), RNA number (c: a control group, d: the present invention), and copy number of neo gene as a selective marker (e: a control group, f: the present invention) in positive clones expressing β-Gal (hereinafter referred to as "positive clones") for pSV-β-gal or pMS-β-gal vector. FIG. 7 is a graph showing the relation between the copy number of the β-Gal gene and the expression yield of β-Gal in positive clones for the pSV-β-gal or pMS-β-gal vector. Since the copy number of the β-Gal gene in each positive clone varied as shown in FIGS. 6a and 6b, each positive clone was classified in two groups, where one has a high copy number of the β-Gal gene, and the other has a low copy number of the β-Gal gene, relatively, and the groups were analyzed with each other. In the group having a high copy number of the β-Gal gene, though control group had a high copy number of the β-Gal gene as shown in "a", the RNA amount of the β-Gal gene in these clones was low relative to DNA copy number as shown in "c". However, the RNA amount in positive clones for pMS-β-gal of the present invention represented in "d" was high. In addition, in the group having a low copy number of the β-Gal gene, the copy number of the β-Gal and the RNA amount in positive clones for the pMS-β-gal vector were much higher than those in positive clones for the control vector, as shown in FIG. 6. FIG. 7 shows the relation between the copy number and the expression amount of the genes. In FIG. 7, the mean copy number and expression level of the β-Gal gene in pMS-β-gal vector clones (●) correspond about 10 times compared to control vector clones (○). In addition, in the case of the high-copy group of the β-Gal gene, the expression of the β-gal gene in control vector clones is independent of the copy number of the gene, and pMS-β-gal as shown in FIG. 7.

(3) Expression Pattern of the pMS-β-gal Vector in Various Cell Lines

In the expression of the foreign genes in animal cells, various kinds of cells as well as CHO are also used, and the expressed amount of foreign genes was various in the various kinds of cells. In the present invention, the expression titer and the expression frequency of the foreign gene in transfected CHO cells increased, when the pMS-β-gal vector in a CHO cell host is used. Therefore, it was tested whether the vector of the present invention is applicable to animal cells of which the origination and morphology are unlike that of the CHO cells.

After the pSV-β-gal vector and the pMS-β-gal vector were respectively co-transfected into a baby hamster kidney cell (BHK), a mouse fibroblast cell (NIH3T3), and a human embryonic kidney cell (HEK293) with a pSV2neo vector, and cultivated in media including G418 for about 14 days, the frequency of positive cells expressing β-Gal and the expression titer in stable transfectants for each vector were measured in the same manner as in (2).

Figure 8:
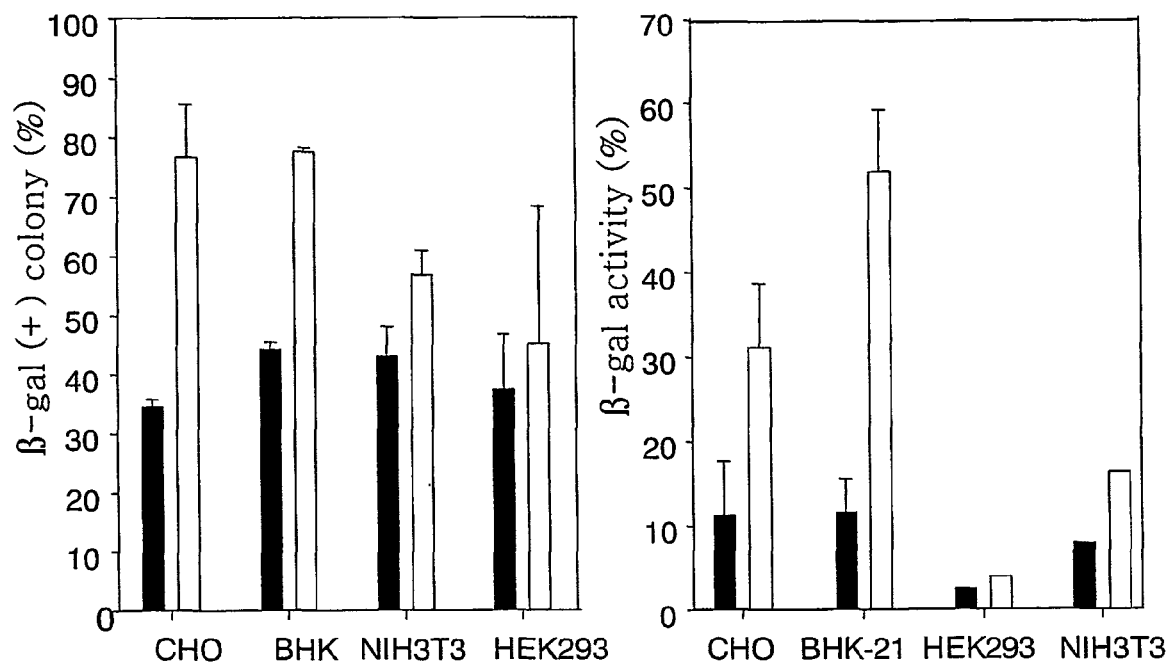
FIG. 8 shows the expression titer of the pMS-β-gal vector in various cell lines.
Figure 9:
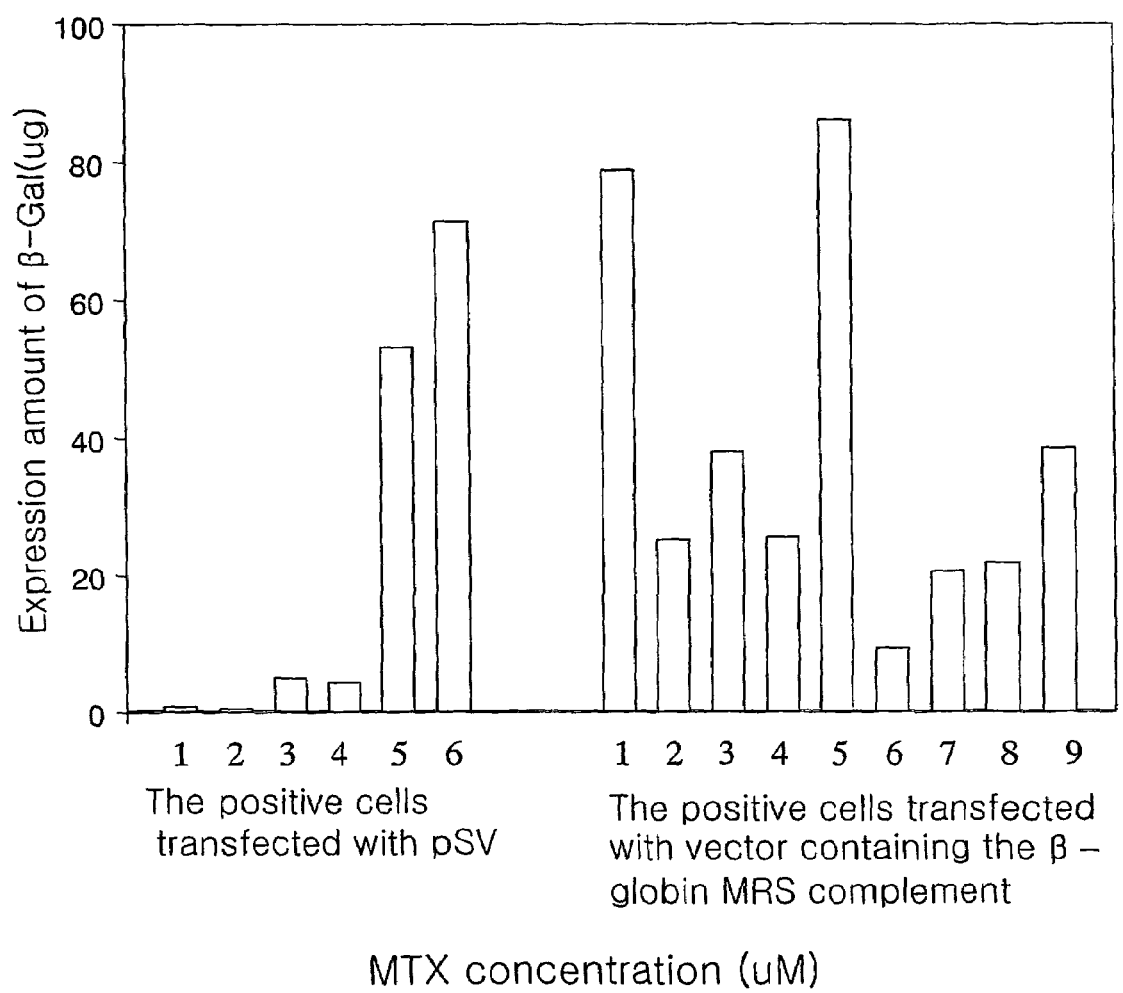
FIG. 9 shows the expressed amount of foreign protein relative to MTX concentration in cells transformed with pMS-β-gal vector or a control vector.

FIG. 8 shows the expression titer of the pMS-β-gal in the various cell lines. When BHK is used for a host cell line, the gene expression is similar to that in a CHO cell line. When NIH 3T3 is used for a host cell line, the effect on the increase of the expression amount was low. When HEK 293 is used for a host cell, the effect and amount of expression was similar to those of the control. The frequency of positive clones was similar to the aforementioned. Therefore, the effects of the expression vectors of the present invention are varied in the kind of cells, and in particular, they are useful for CHO, BHK, and NIH 3T3 cells which are generally used in the expression of animal cells.

(4) Establishment of Expression System of the pMS-β-gal Vector.

In the conventional expression vector system, highly expressing clones should be selected through tedious processes to isolate as many as possible in pooled primary transfectants, and to cultivate these clones for a long time to increase the expression level of foreign genes. In order to overcome these problems and maximize the expression level of foreign genes, the DHFR/MTX amplification system was established using the CHO DG44 cell line.

The pMS-β-gal vector was transfected into the DHFR—CHO DG44 (hereinafter referred to as "CHO DG44") cell line, transfectants for pMS-β-gal vector were adapted to MTX and then the expressed amount of the proteins was measured. The pMS-β-gal vector and the control (the pSV-β-gal vector) were respectively co-transfected into CHO DG 44 lacking DHFR genes with the pDCH1P vector having DHFR genes. The DHFR-transfected cell strains were cultivated in selective media, MEM-α medium lacking nucleosides supplemented 10% heat-inactivated dialyzed FBS. Stable DHFR$^+$ transfectants were generated after about 2 weeks, and the positive clones expressing β-Gal in stable DHFR$^+$ transfectants were isolated by β-Gal staining. For the β-Gal staining to screen positive clones expressing β-Gal in DHFR$^+$ transfectants, cells were fixed by incubating in PBS containing 2% formaldehyde, and 0.2% glutaraldehyde at 4° C. for 10 minutes, washed twice with PBS, and treated with X-Gal. When β-Gal is expressed, the cell appears blue since blue products are generated due to the decomposition of X-Gal by the β-Gal protein. The selected clones were treated in multiple stepwise increments of MTX concentration such as 10 nM, 20 nM, 50 nM, 100 nM, 400 nM, and 1 µM. It took clones about 2 to 3 weeks to adapt to each MTX concentration cultivated. The expressed amount of β-Gal during gene amplification by MTX adaptation was analyzed with the conventional ELISA.

FIG. 9 shows the expressed amount of recombinant proteins in cells transfected with pMS-β-gal and the control, respectively, and adapted to 1 µM MTX concentration. It has been reported that when the expression of recombinant proteins was amplified by the DHFR.MTX amplification system in the CHO cell line, the expression level was up to about 10 µg/$10^6$ cells/day which corresponds to 2.5% of the total proteins (Kaufman, 1997, Methods Mol Biol 62, 287–300). In the present invention, it is observed that about 100 to 1000 of copy numbers are amplified by gradually increasing the MTX amount. The expressed amount of β-Gal in clones for the pMS-β-gal vector of control was measured. The expression amount of β-Gal in control clones is varied with each clone. Considered that 20 µg/$10^6$ cells is valuable industrially in recombinant protein production in animal cells, 25% of control vector clones belong to that, and 88% of pMS-β-gal vector clones of the present invention produced the recombinant protein above 20 µg/$10^6$ cells. Compared to cell strains having maximal expression amount, pMS-β-gal of the present invention has a large amount of expressed protein, and large amounts of proteins can be produced by inserting a foreign gene into pMS (KCCM-10203). Therefore, when the expression vector of the present invention is used for expression of foreign genes, it results in a high expression yield and efficiency.

EXAMPLE 2

Preparation of pSPUK, pMSPUK, pCPUK, and pMCPUK (1) Preparation of pCMV Vector

A pCMV vector was prepared in order to make cloning of a CMV promoter and a SV40 promoter to scu-PA genes easy. A PCR for obtaining the CMV promoter, MCS site, and a transcriptional termination site of pcCDNA 3.1 (+) (a product by Invitrogen Co.) was performed. A PCR sense primer is CMVL1 (SEQ ID No. 11), and an antisense primer is PAR1 (SEQ ID No. 12). The CMVL1 primer has Sac II, Cla I, Nru I sites, and the PAR1 primer has BsmI site. After a 1.4 kb of PCR product was digested with the Sac II and Bsm I, it was ligated with a linearized recombinant pSV-g-gal version I in order to prepare pCMV.

(2) Preparation of pSPUK, pMSPUK, pCPUK, and pMCPUK

In order to prepare a recombinant expression vector for scu-PA expression in an animal cell, scu-PA genes are obtained by PCR from the genomic DNA separated from a CHO cell strain having scu-PA genes originated from a human TCL-598 cell strain as a template. A sense primer PKL1 is filed as SEQ ID No. 13, and an antisense primer PKR1 is filed as SEQ ID No. 14. The PKL1 primer has a Hind III restriction site, and the PKR1 primer has a Sma I restriction site.

About 1.3 kb of scu-PA PCR product produced from the primers (a DNA fragment having a base No. −6 to a base No. 1293 of a human scu-PA) was cut by Sma I and Hind III, and inserted into a plasmid, pCMV which is cut by Hind III and EcoR V in order to prepare a pCPUK expression vector.

In addition, the recombinant pSV-β-gal version I vector was treated with Sma I and Hind III in order to separate a fragment having the SV40 promoter. This fragment was inserted into and joined with a pCPUK of control which is linearized by Nru I and Hind III in order to prepare a pSPUK expression vector.

The pCPUK was treated with Sac II and Nru I in order to insert the MAR element into it. The linearized pCPUK was inserted into and joined with a β-globin MAR element which was prepared by treating the pMS-β-gal vector with Sma I and SacII, in order to prepare a pMCPUK vector.

The pSPUK vector was treated with Stu I and Sac II in order to insert a β-globin MAR element into it. A β-globin MAR element, which was produced by treating pMS-β-gal vector with Su I and Sac II, was inserted to the pSPUK vector, and the pMSPUK vector was prepared.

In brief, the pSPUK vector construct was the form produced by inserting the scu-PA gene into the recombinant vector, pSV-β-gal version I of which the β-Gal gene was removed, and the β-globin MAR complementary sequence was inserted into the pSPUK vector in order to prepare the pMSPUK vector. A pCPUK vector construct was the form produced by inserting scu-PA into the pCMV vector, and the β-globin MAR complementary sequence was inserted into pCPUK in order to prepare a pMCPUK vector.

(3) Test for Efficiency of the pSPUK, pMSPUK, pCPUK, and pMCPUK Vectors

①Transfection of Recombinant scu-PA Genes into a Cell, Selection of Transformants and Amplification of the Gene Four kinds of recombinant expressing plasmids, that is pSPUK, pMSPUK, pCPUK, and pMCPUK, were respectively introduced into DHFR—CHO cells (CHO DG44) in order to obtain a cell line stable enough to express scu-PA. 2×$10^5$ CHO cells were placed in a 6-well plate, and incubated in a 5% $CO_2$ incubator at 37° C. for 24 hours. 1 µg of the plasmids of the pSPUK, pMSPUK, pCPUK and pMCPUK and 10 ng of DHFR minigene were respectively mixed in a ratio of 100:1, and the mixture was transfected into the CHO cell by the method of lipofectamine, (GiboBRL), or DOSPER (Loche). After 6 hours, a medium was replaced with fresh culture medium, and the cells were further incubated for 48 hours. The cells were subcultured on the medium to the selective medium in a ratio of 10:1 for about 2 weeks or more, and the medium was exchanged per about four or five days in order to form a cell colony. The cell colony was cultivated separately or together.

② Activity Measurement of scu-PA Secreted to the Culture Solution for Cells

The amidolytic activity of the culture medium of cells, which was measured by use of S-2444 as a substrate, was compared to reference urokinase activity. $1\times10^6$ cells were placed in a 6-well plate with 2 ml of the culture solution, and cultivated in a 5% $CO_2$ incubator at 37° C. for 17 hours. In order to measure the activity of the supernatant, 50 μl of the serially diluted supernatant was placed in a 96-well plate, and mixed with 30 μl of buffer solution (50 mM Tris/HCl (pH 8.8), 80 mM NaCl, 0.02% Twin 80). 10 μl plasmin (0.5 U/ml) was further mixed to the mixture, and the mixture was reacted at 37° C. for 20 minutes in order to activate the recombinant scu-PA. 10 μl aprotinin (100 KIU/ml) was added to the mixture in order to inhibit plasmin activity, and 100 μl chromogenic substrate solution (a mixture of the buffer solution and 6 mM of S-2444) was further added to the mixture, and reacted at 37° C. for 1 hour. The activity and the concentration of the scu-PA in the culture medium were measured by absorbance (optical density) measurement at 405 nm of the resulting solution with a microplate reader, and the results were compared to that of urokinase as a reference.

FIG. 10 shows the expression titer of the scu-PA according to transfecting pMSPUK, pMCPUK, pSPUK and pCPUK into CHO cells. The expression level from the pMS and pMC vectors increased by 4 times more than that from pSV and pCMV as control.

EXAMPLE 3

Preparation of pSG-β-gal Vector (1) Preparation of the Transcription Termination Site of the Gastrin Gene and the pSG-β-gal Vector After the sense strand of the transcription termination site of gastrin genes of SEQ ID No. 15 was synthesized, and an antisense strand of SEQ ID No. 16 was synthesized, the two were annealed. The annealing fragment was treated with BamH I and Pst I, and integrated into and joined with linearized pSV-β-gal vector (a vector produced by Promega Co.) by BamH I and Pst I digestion at the 3' of the SV40 p(A) terminator, so that pSG-β-gal was prepared.

(2) Measurement of the pSG Vector Efficiency

The pSG-β-gal vector was co-transfected into Cos-7 cell with a pSV2neo vector by using DOSPER (Roche), in order to measure the expression titer of β-Gal.

Figure 12:
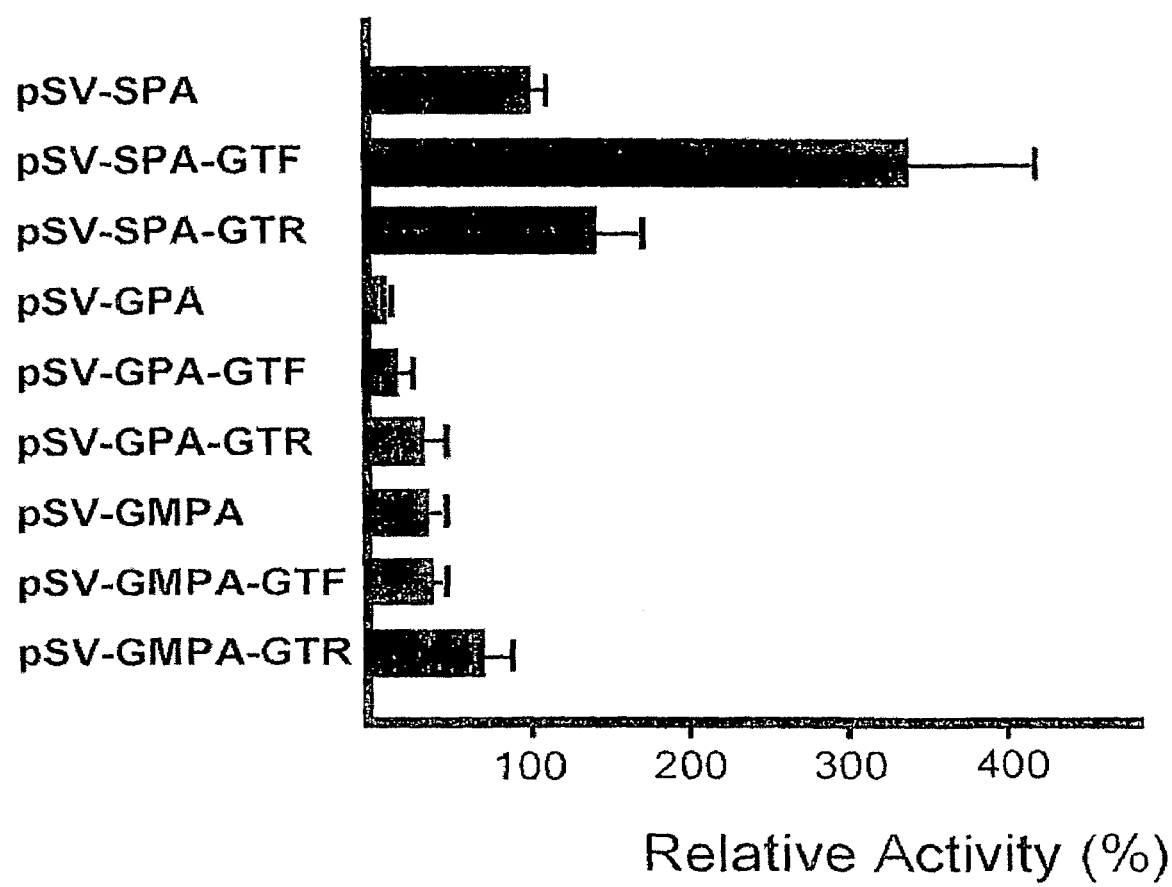
FIG. 12 shows the expressed amount of β-Gal in an expression vector comprising a construct including the transcription termination site of the gastrin gene and the SV40 poly-A signal.

FIG. 12 shows the expression titer of β-Gal in the pSG-β-gal vector. The pSG-β-gal vector comprising the construct consisting of the SV40 poly-A and the transcription termination site of the gastrin gene produces β-Gal by 4 times more than that of the conventional vector comprising SV40 poly-A. Therefore, a large amount of recombinant protein can be produced by the transfection of foreign genes cloned in the pSG vector.

EXAMPLE 4

(1) Preparation of the pMSG Vector

As shown in FIG. 13, a vector containing the β-globin MAR complementary sequence and SPA-GTF was prepared by the PCR. In order to prepare the pMSG vector, the pMS-β-gal and the pSG-β-gal were used as templates, the PCR was performed three times, and the PCR producer was treated with a specific restriction enzyme, and joined together.

① PCR of the β-globin MAR Element

A sense primer ML1 (SEQ ID NO: 17) and an antisense primer MR1 (SEQ ID NO: 18) were used for the PCR. After the PCR product was treated with Sac II and Cla I, it was integrated with the linearized pMS-β-gal vector by Sac II and Cla I digestion, and the pMS-β-gal/sc vector was prepared.

② PCR for Obtaining Multicloning Sites and Transcriptional Termination Sites

A sense primer TL1 (SEQ ID NO: 19) and an antisense primer TR1 (SEQ ID NO: 20) were used in PCR for the transcription termination site of the gastrin gene of the pSG vector. The PCR product was sub-cloned with pGEM-T (a product by Promega Co.), which is a sort of TA cloning vector which is capable of cloning a PCR product directly, so that pGEM-T/MCSp(A) was prepared.

③ PCR for Obtaining SV40 Promoter and Multicloning Site

A sense primer PL1 (SEQ ID NO: 21) and an antisense primer PR1 (SEQ ID NO: 22) were used in the PCR for the SV 40 promoter and the multi-cloning site of the version 1 vector of FIG. 1. The PCR product was treated with Apa I and Bgl II, and then integrated with linearized pGEM-T/MCSp(A) vector by Apa I and Bgl II digestion, so that the pGEM-T/SVMCSp(A) vector was prepared.

④ Preparation of pMS Vector and pMSG Vector

PGEM-T/SVMCSp(A) of Example 4 was treated with Apa I and BamH I in order to purify a DNA fragment consisting of the SV40 promoter, multicloning sites, and a SV40 termination site, and the purified fragment was integrated into linearized pMS-β-gal/sc vector by Apa I and BamH I digestion of ① in Example 4, so that the pMS vector was prepared. The pSG vector was treated with BamH I and Sca I in order to separate a 950 bp DNA fragment having the GTF base sequence. It was joined with the linearized pMS vector by BamH I and Sca I digestion, so that a pMSG vector was prepared.

(2) Measurement of Expression Titer in PMSG Vector

The PCR for the TFG-β SRII (TGF-β soluble receptor II, glycosylation protein) gene was performed with a sense primer TR1 (SEQ ID No.23) and an antisense primer TRR1 (SEQ ID No. 24) in order to verify the expression efficiency of the pMSG vector in a CHO host cell line and the industrial application of the pMSG vector. The PCR product, amplified TGF-β SRII, was inserted into the pMSG and pSV vectors at Nhe I and Xho I sites, and each resultant vector was co-transfected into CHO DG44 cells with pDCH1P having DHFR genes. They were cultivated in selective media, where only a cell strain having DHFR genes could be grown. Stable DHFR$^+$ transfectants were generated after about 2 weeks, twenty DHFR$^+$ clones were isolated, and these clones were analyzed by the western blot in order to measure the amount of TGF-β SRII and find its characteristics.

Figure 14:
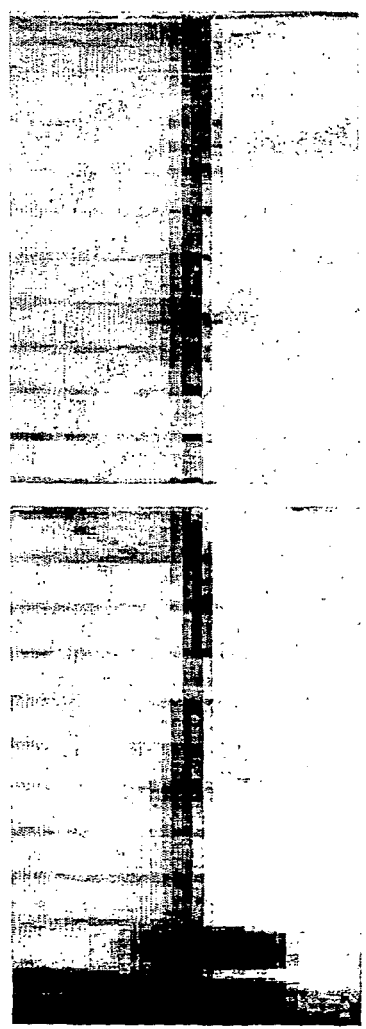
FIG. 14 shows the expression of the TGF-β SRII in the pMSG vector confirmed by an antigen-antibody reaction.
Figure 14:
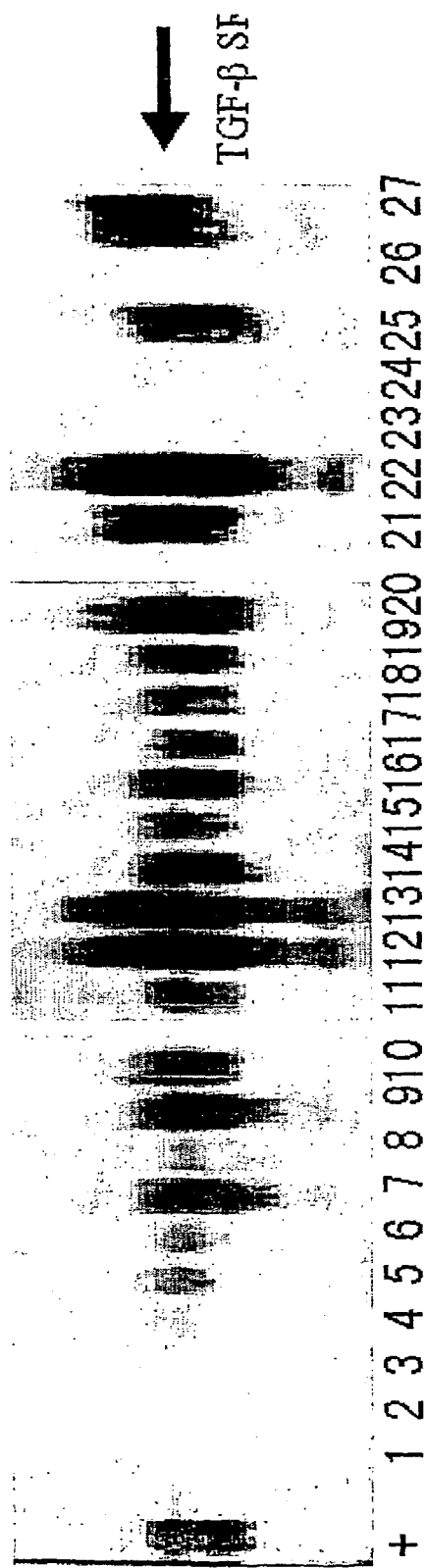
Figure 15:
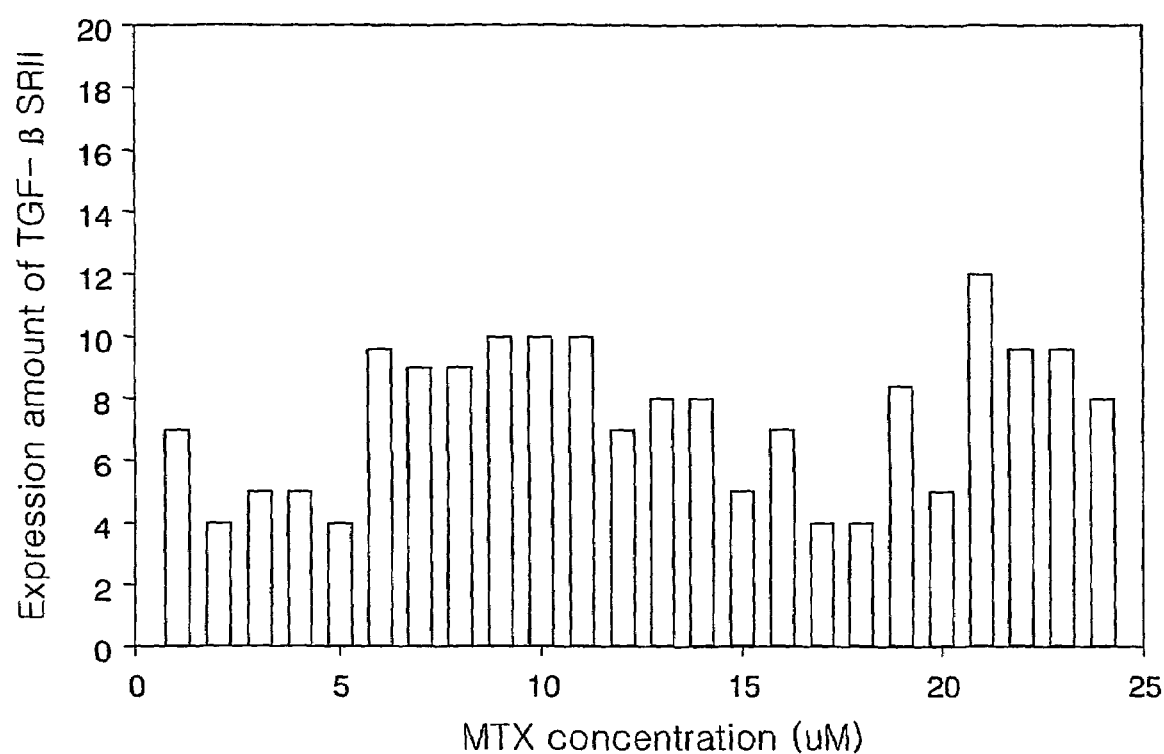
FIG. 15. shows the expressed amount of the TGF-β SRII which is produced by cloning the TGF-β SRII gene into the pMSG vector, transfecting into CHO cells, and culturing in MTX.

FIG. 14 shows a western blot that indicates TGF-β SRII expression, wherein "a" is the TGF-β SkII expressed from the pSV vector clones, and "b" is the TGF-β SRII expressed from the pMSG vector clones. In case of control vector clones, TGF-β SRII expression in one clone among 25 clones was detected, whereas in 23 clones among 27 clones expression of TGF-β SRII was detected. Further more many clones expressed TFG-β at high levels. In addition, when TGF-β SRII was expressed by the pMSG expression vector, it had a glycosylation structure, so that its molecular weight increased as a glycoprotein of a typical animal cell. The average expression level of these primary clones for pMSG vector is about 100 ng/$10^6$ cells/day.

The stable primary clones for the pMSG/TGF-β SRII vector of the present invention were adapted to the DHFR/MTX amplification system by treatment in multiple stepwise increments of MTX in an amount such as 10 nM, 40 nM, 200 nM, and 1 μM, in order to increase the expression of the TGF-β SRII.

FIG. 15 shows an expressed amount of TGF-β SRII which is produced by cloning the TGF-β SRII into the pMSG vector, transfecting them in a CHO cell, and adapting to 1 μM MTX concentration. In the control vector clones, many clones are not adapted at each MTX concentration during the gene amplification process by MTX treatment, whereas the pMSG/TGF-β SRII vector clones are well adapted, compared to the control vector clones. It is supposed that the MAR element of the pMSG expression vector increases the expressed amount of the DHFR genes as well as foreign genes. As shown in FIG. 15, when adapted to 1 μM MTX concentration, many clones for the pMSG vector which is produced TGF-β in about 10 μg/$10^6$ cells/day were obtained.

It has been reported that TGF-β, a potent regulator of cell growth and differentiation, is central to the injury response. In a number of epithelia, repeated or prolonged injury leads to progressive fibrosis and ultimately the development of unwanted excessive scarring. In addition, TFG-β results in disease such as corpora glomerulus, sclerosis of kidney, hepatic cirrhosis, cornification of epidermal cells, and an inflammatory cartilage. TFG-β SRII functions as an antagonist of TFG-β. Therefore, TGF-β is prohibited by the treatment of the TGF-β SRII as a medical treatment. The TGF-β SRII expressed from a CHO cell line of the present invention has an excellent treatment effect compared to the proteins which are expressed from a prokaryote such as *E. coli*, or *Pichia pastoris*, and the expression vector of the present invention, which has an improved expression titer of the foreign genes, may be used in animal cells.

The invention claimed is:

1. An expression vector for an animal cell selected from the group consisting of a CHO, a BHK, an NIH 3T3, and a Cos-7 cell, comprising a promoter selected from the group consisting of a SV40 virus promoter and a CMV promoter; and a β-globin MAR (nuclear matrix attachment region) element or its complement at the 5'-terminal end of the promoter, wherein the expression vector for animal cells is the pMS vector of SEQ ID NO:1.

2. An expression vector for animal cells comprising the sequence of SEQ ID NO:3.

3. The expression vector according to claim 2, wherein the expression vector is the pSG vector of SEQ ID NO:7.

4. An expression vector for an animal cell selected from the group consisting of a CHO, a BHK, an NIH 3T3, and a Cos-7 cell, comprising a promoter selected from the group consisting of a SV40 virus promoter and a CMV promoter; and a β-globin MAR (nuclear matrix attachment region) element or its complement at the 5'-terminal end of the promoter, and further comprising the sequence of SEQ ID NO:3 as a terminator.

5. The expression vector according to claim 4, wherein the expression vector is the pMSG vector of SEQ ID NO:8.

* * * * *

SEQUENCE LISTING

```
<160> NUMBER OF SEQ ID NOS: 24

<210> SEQ ID NO 1
<211> LENGTH: 6287
<212> TYPE: DNA
<213> ORGANISM: Artificial Sequence
<220> FEATURE:
<223> OTHER INFORMATION: pMS vecter sequence
<220> FEATURE:
<221> NAME/KEY: promoter
<222> LOCATION: (1)..(419)
<223> OTHER INFORMATION: SV40virus
<220> FEATURE:
<221> NAME/KEY: gene
<222> LOCATION: (3305)..(6269)
<223> OTHER INFORMATION: Human beta globin MAR element

<400> SEQUENCE: 1
gcgcagcacc atggcctgaa ataacctctg aaagaggaac ttggttaggt accttctgag      60
gcggaaagaa ccagctgtgg aatgtgtgtc agttagggtg tggaaagtcc ccaggctccc     120
cagcaggcag aagtatgcaa agcatgcatc tcaattagtc agcaaccagg tgtggaaagt     180
ccccaggctc cccagcaggc agaagtatgc aaagcatgca tctcaattag tcagcaacca     240
tagtcccgcc cctaactccg cccatcccgc cctaactccg cccagttcc gcccattctc      300 cgccccatgg ctgactaatt ttttttattt atgcagaggc cgaggccgcc tcggcctctg     360
agctattcca gaagtagtga ggaggctttt ttggaggcct aggcttttgc aaaaagcttg     420
ctagcggccg cagatctgtt aactcgagaa cttgtttatt gcagcttata atggttacaa     480
ataaagcaat agcatcacaa atttcacaaa taaagcattt ttttcactgc attctagttg     540
tggtttgtcc aaactcatca atgtatctta tcatgtctgg atcctctaga gtcgacctgc     600
aggcatgcaa gctggcactg gccgtcgttt tacaacgtcg tgactgggaa aaccctggcg     660
ttacccaact taatcgcctt gcagcacatc cccctttcgc cagctggcgt aatagcgaag     720
aggcccgcac cgatcgccct tcccaacagt tgcgcagcct gaatggcgaa tggcgcctga     780
tgcggtattt tctccttacg catctgtgcg gtatttcaca ccgcatatgg tgcactctca     840
gtacaatctg ctctgatgcc gcatagttaa gccagccccg acacccgcca cacccgctg      900 acgcgccctg acgggcttgt ctgctcccgg catccgctta cagacaagct gtgaccgtct     960
ccgggagctg catgtgtcag aggttttcac cgtcatcacc gaaacgcgcg agacgaaagg    1020
gcctcgtgat acgcctattt ttataggtta atgtcatgat aataatggtt tcttagacgt    1080
```

```
caggtggcac ttttcggggga aatgtgcgcg gaacccctat ttgtttattt ttctaaatac    1140
attcaaatat gtatccgctc atgagacaat aaccctgata aatgcttcaa taatattgaa    1200
aaaggaagag tatgagtatt caacatttcc gtgtcgccct tattccctttt tttgcggcat   1260 tttgccttcc tgtttttgct cacccagaaa cgctggtgaa agtaaaagat gctgaagatc    1320
agttgggtgc acgagtgggt tacatcgaac tggatctcaa cagcggtaag atccttgaga    1380
gttttcgccc cgaagaacgt tttccaatga tgagcacttt taaagttctg ctatgtggcg    1440
cggtattatc ccgtattgac gccgggcaag agcaactcgg tcgccgcata cactattctc    1500
agaatgactt ggttgagtac tcaccagtca cagaaaagca tcttacggat ggcatgacag    1560
taagagaatt atgcagtgct gccataacca tgagtgataa cactgcggcc aacttacttc    1620
tgacaacgat cggaggaccg aaggagctaa ccgcttttt gcacaacatg ggggatcatg    1680
taactcgcct tgatcgttgg gaaccggagc tgaatgaagc cataccaaac gacgagcgtg    1740
acaccacgat gcctgtagca atggcaacaa cgttgcgcaa actattaact ggcgaactac    1800
ttactctagc ttcccggcaa caattaatag actggatgga ggcggataaa gttgcaggac    1860
cacttctgcg ctcggccctt ccggctggct ggtttattgc tgataaatct ggagccggtg    1920
agcgtgggtc tcgcggtatc attgcagcac tggggccaga tggtaagccc tcccgtatcg    1980
tagttatcta cacgacgggg agtcaggcaa ctatggatga acgaaataga cagatcgctg    2040
agataggtgc ctcactgatt aagcattggt aactgtcaga ccaagtttac tcatatatac    2100
tttagattga tttaaaactt cattttaat ttaaaaggat ctaggtgaag atcctttttg    2160
ataatctcat gaccaaaatc ccttaacgtg agttttcgtt ccactgagcg tcagaccccg    2220
tagaaaagat caaaggatct cttgagatc cttttttttct gcgcgtaatc tgctgcttgc    2280
aaacaaaaaa accaccgcta ccagcggtgg tttgtttgcc ggatcaagag ctaccaactc    2340 ttttttccgaa ggtaactggc ttcagcagag cgcagatacc aaatactgtc cttctagtgt   2400
agccgtagtt aggccaccac ttcaagaact ctgtagcacc gcctacatac ctcgctctgc    2460
taatcctgtt accagtggct gctgccagtg gcgataagtc gtgtcttacc gggttggact    2520
caagacgata gttaccggat aaggcgcagc ggtcgggctg aacggggggt tcgtgcacac    2580
agcccagctt ggagcgaacg acctacaccg aactgagata cctacagcgt gagctatgag    2640
aaagcgccac gcttcccgaa gggagaaagg cggacaggta tccggtaagc ggcagggtcg    2700
gaacaggaga gcgcacgagg gagcttccag ggggaaacgc ctggtatctt tatagtcctg    2760
tcgggtttcg ccacctctga cttgagcgtc gattttttgtg atgctcgtca gggggggcgga   2820 gcctatggaa aaacgccagc aacgcggcct ttttacggtt cctggccttt tgctggcctt    2880
ttgctcacat gttctttcct gcgttatccc ctgattctgt ggataaccgt attaccgcct    2940
ttgagtgagc tgataccgct cgccgcagcc gaacgaccga gcgcagcgag tcagtgagcg    3000
aggaagcgga agagcgccca atacgcaaac cgcctctccc cgcgcgttgg ccgattcatt    3060
aatgcagctg gcacgacagg tttcccgact ggaaagcggg cagtgagcgc aacgcaatta    3120
atgtgagtta gctcactcat taggcacccc aggctttaca cttatgcttc cggctcgta    3180 tgttgtgtgg aattgtgagc ggataacaat ttcacacagg aaacagctat gaccatgatt    3240
acgccaagct cgaaattaac cctcactaaa gggaacaaaa gctggagctc caccgcggcc    3300
cgggcctcct gagtagctgg gactacaggt gtacatcaca tgcctggcta attttttttt    3360
tttaagtaga cgagggtct tgctatgttg tccaggataa tatcaaactc ttgagctcaa    3420
gcagtcctcc cacttctacc tctcaagtgc tggaattaca gacatgagcc accactcctg    3480
```

```
gcttgcagac tatttaaatg actaattcct gacactgctt gagggatact agacagtaga    3540
caacacatct ttaatatacc aaatgggtga ctgtagggtt gagagggaga ttagaattca    3600
atgttttatg accaaaaagg cttaaatcag gcacaagctt aggtcttttc aactgtgagg    3660
accggactga aagtgtgcag ttcaaggccc tgtagttgct gtttaactgt tcccaggtgg    3720
aagtctcttc aaagaaccac tggtgcaaaa agggaactac ctggggataa atatttcctc    3780
cagaaagggg gaaagtgcaa gctcccctac caaaagcacc aggcaagtcc ttgtctattt    3840
tccctgaagt tctcaaagaa atgagaccct tgtttacctt taagattaga gaaggcttga    3900
aaagtttgag ctgtgccttt ggaggccaac aaacttttct cctttgttga ccaagttcag    3960
ctctcctgta tacttccaag gtctgttgca tcaagagtga gaattgaagg tcttagaagc    4020
tgggatctca gatgtaggga aaagaggaga tttcctgttc actcactgtt aagatatggc    4080
tgaaattttt tgatctagtc atctacaaag catgagttgt gggtcagaaa ttgttttttca    4140
catcttttga cttcctttga catcagaata taacctagga attgattact taagtgaagg    4200
caaggtactt tggtctggac aggaacattt tgaacaaggt agggagacag ctatgaaggc    4260
aagcatttat tctatctatc atctatctgt ctatctatct attctttcat ccacttattt    4320
atacatttaa acaaaaagta tagagcgtag tataatttgt aagtgctcag ggctgtgtgt    4380
gtatggattg tttgaaatga aactaaagtg ggagtataat tctactgccc ccttaacccct   4440
gtggtcccta cactaccctg caagactctt agctgcttag cttaattgtg aggctgattt    4500
ggggcatagc acccatcctc tctgtctttc aacatcctca taataacttg agataatttt    4560
ataaaatatc acaataggt catgttcagt agggtgatat ataaaattag acaagccata    4620
gtttgagtta cccttttgaa taaatatatg acaaaaggca atttaattat ctttatgagt    4680
ttggaggtat ccagtatgaa atttagataa tacctgcctt ctagtgttga aattagaact    4740
taatgatata atgcatcaat gaacttatta tagttcctag cacaaagtaa gaatcctttc    4800
aatgtgtgtg tgtgtgtatg tatttatctg ttattaatag gaatcttata gggcattatc    4860
tcacttaatc cttattaata actatgaagc aggtatttat ttgagttttc caagtgagtt    4920
aagtatagct tgtaatactt aaggaaatat ccacaggtta catagctagt atataactga    4980
gaaataattt tatttatatt ataaaacatt ctaacaatac agatgtatat aaactaaaaa    5040
actgaaaggg ctcatgcaac cctaccttct caatatcact tcttcactta gaaaaaacca    5100
gccttagctg tctgctatga atcctttcaa aatatacttc tgagaaatga gagagagaaa    5160
tggggagggt agaaggaagg aagatagggt aagagacagg gaaggaggtg tggggaaaga    5220
aattaaatta ttcttttctc tgtctcttga aagagctctt tccattacat tgaatcaaag    5280
gtaatgttgc catttctgga ctcttgaaat aaagaaagac cgatgtatga aataattttg    5340
aaagtctatg gcattttcaa aatgcaaggt gatgtcttac taactagcct ttgctttatt    5400
attagaaatg gggaagtgag tatagacatt ttatcaggag atatattagg aaaaagggaa    5460
actggagaaa ctgggaggag tatccagatg tcctgtccct gtaaggtggg ggcacccacc    5520
ttcaatcaaa agggctcctt aacaacttcc ttgcttgggg ctccaccatc ttggaccatt    5580
agctccacag gtatcttctt ccctctagtg gtcataacag cagcttcagc tacctctcta    5640
aagagtcctg ccagatatag gtcaggaaat ataaccacta ataaaagag aaacattttg     5700
actgtagttg tttgttttt gtcattgtga ctatcaataa cattctcact ctttcatcag     5760
taatcactca ggttattctg tgaccaacag actgtgggaa aaatcagaga aggaggcatc    5820
```

```
ctcatgctta ctagcctaaa ctgaaattgc tatagcagag tgaaccagaa ggtttacaga      5880
tattttccac aaagagtaaa aggattgaag ccttctccag atcaatgcat aggaaataat      5940
aatggaccat aaaacccata ttatgacgaa caacattagg ataagtccat atcaattttt      6000
aatccagtca taagcacaga ctacgtgaag cacgtccaag tgaaggcagg agaaatgaga      6060
ggagcaagaa agaggagcca tttgatcaag aatagcagaa aaaggaaagg caagtcatat      6120
taacaaatga ttgtcatgcc aacagtacag ataactctgc taataaaggt agaggcataa      6180
tacaggtagt agcagatatc tacatagtag ttaaaggaca tggccatcag tacagaagat      6240
tccataaagg agaacctaaa gaggaagaaa tcgataagct tgatccc                   6287
```

<210> SEQ ID NO 2
<211> LENGTH: 435
<212> TYPE: DNA
<213> ORGANISM: Artificial Sequence
<220> FEATURE:
<223> OTHER INFORMATION: gastrin fragment which is digested by Hind III
      restriction enzyme, cotaining poly-a signal, termination code
<220> FEATURE:
<221> NAME/KEY: terminator
<222> LOCATION: (256)..(435)

<400> SEQUENCE: 2

```
taacaatcct agaaccaagc ttcagagcct agccacctcc cacccacct ccagccctgt        60 cccctgaaaa actgatcaaa aataaactag tttccagtgg atcaatggac tgtgtcagtg      120
ttgtagggca aggaggggg actcatctgg gctcatctgg gggtgaagtt gtggcaggga      180
ctaagagctg agtgcctctt aggggcaggg accgtcccc agagcccac attgaacgag        240 aatccacagg tatgggcagg ataatatatg gtagggttca tagccagagt aaccttttt      300 tttaattttt attttatttt attttgaga tggagtttcg ctcttgtctc ccaggctgga      360
gtgcaataat gagacctcag ctcactgcaa cctctgcctc ctaggttcaa gcgattttcc      420
tgcctcagcc tccca                                                       435
```

<210> SEQ ID NO 3
<211> LENGTH: 214
<212> TYPE: DNA
<213> ORGANISM: Artificial Sequence
<220> FEATURE:
<223> OTHER INFORMATION: SV 40 virus poly-A signal and gastrin
      termination site
<220> FEATURE:
<221> NAME/KEY: polyA_signal
<222> LOCATION: (1)..(135)
<220> FEATURE:
<221> NAME/KEY: terminator
<222> LOCATION: (136)..(214)

<400> SEQUENCE: 3

```
aacttgttta ttgcagctta taatggttac aaataaagca atagcatcac aaatttcaca       60
aataaagcat ttttttcact gcattctagt tgtggtttgt ccaaactcat caatgtatct     120
tatcatgtct ggatccagga taatatatgg tagggttcat agccagagta acctttttt      180 ttaatttta ttttatttta ttttgagct gcag                                   214
```

<210> SEQ ID NO 4
<211> LENGTH: 221
<212> TYPE: DNA
<213> ORGANISM: Artificial Sequence
<220> FEATURE:
<223> OTHER INFORMATION: SV40 virus poly-A signal and reverse of gastrin
      poly-A signal

```
<220> FEATURE:
<221> NAME/KEY: polyA_signal
<222> LOCATION: (1)..(137)
<220> FEATURE:
<221> NAME/KEY: terminator
<222> LOCATION: (138)..(221)

<400> SEQUENCE: 4
aacttgttta ttgcagctta taatggttac aaataaagca atagcatcac aaatttcaca      60
aataaagcat ttttttcact gcattctagt tgtggtttgt ccaaactcat caatgtatct    120
tatcatgtct ggatcaactg cagctcaaaa ataaaataaa ataaaaatta aaaaaaaagg    180
ttactcaggc tatgaaccct accatatatt atcctgcagt t                       221

<210> SEQ ID NO 5
<211> LENGTH: 217
<212> TYPE: DNA
<213> ORGANISM: Artificial Sequence
<220> FEATURE:
<223> OTHER INFORMATION: SV40 virus poly-A signal and gastrin poly-A
      signal
<220> FEATURE:
<221> NAME/KEY: polyA_signal
<222> LOCATION: (1)..(135)
<220> FEATURE:
<221> NAME/KEY: terminator
<222> LOCATION: (136)..(217)

<400> SEQUENCE: 5
aacttgttta ttgcagctta taatggttac aaataaagca atagcatcac aaatttcaca      60
aataaagcat ttttttcact gcattctagt tgtggtttgt ccaaactcat caatgtatct    120
tatcatgtct ggatccggga tcccctgaaa aactgatcaa aaataaacta gtttccagtg    180
gatcaatgga ctgtgtcagt gttgtagggc tgcagtt                            217

<210> SEQ ID NO 6
<211> LENGTH: 217
<212> TYPE: DNA
<213> ORGANISM: Artificial Sequence
<220> FEATURE:
<223> OTHER INFORMATION: SV40 virus poly-A signal and minmal gastrin
      poly-A signal
<220> FEATURE:
<221> NAME/KEY: polyA_signal
<222> LOCATION: (1)..(135)
<220> FEATURE:
<221> NAME/KEY: terminator
<222> LOCATION: (136)..(217)

<400> SEQUENCE: 6
aacttgttta ttgcagctta taatggttac aaataaagca atagcatcac aaatttcaca      60
aataaagcat ttttttcact gcattctagt tgtggtttgt ccaaactcat caatgtatct    120
tatcatgtct ggatccggga tcccctgaaa aactgatcaa aaataaacta gttttttccac   180 tgcattctag ttgtgttagt gttgtagggc tgcagtt                            217

<210> SEQ ID NO 7
<211> LENGTH: 3309
<212> TYPE: DNA
<213> ORGANISM: Artificial Sequence
<220> FEATURE:
<223> OTHER INFORMATION: pSG vecter sequence
<220> FEATURE:
<221> NAME/KEY: promoter
<222> LOCATION: (1)..(419)

<400> SEQUENCE: 7
```

-continued

```
gcgcagcacc atggcctgaa ataacctctg aaagaggaac ttggttaggt accttctgag      60
gcggaaagaa ccagctgtgg aatgtgtgtc agttagggtg tggaaagtcc ccaggctccc     120
cagcaggcag aagtatgcaa agcatgcatc tcaattagtc agcaaccagg tgtggaaagt     180
ccccaggctc cccagcaggc agaagtatgc aaagcatgca tctcaattag tcagcaacca     240
tagtcccgcc cctaactccg cccatcccgc cctaactcc gcccagttcc gcccattctc      300
cgccccatgg ctgactaatt ttttttattt atgcagaggc cgaggccgcc tcggcctctg     360
agctattcca gaagtagtga ggaggctttt ttggaggcct aggcttttgc aaaaagcttg     420
ctagcggccg cagatctgtt aactcgagaa cttgtttatt gcagcttata atggttacaa     480
ataaagcaat agcatcacaa atttcacaaa taaagcattt ttttcactgc attctagttg     540
tggtttgtcc aaactcatca atgtatctta tcatgtctgg atccaggata atatatggta     600
gggttcatag ccagagtaac cttttttttt aattttttatt ttatttatt tttgagctgc     660
aggcatgcaa gctggcactg ccgtcgtttt acaacgtcg tgactgggaa aaccctggcg      720
ttacccaact taatcgcctt gcagcacatc ccccttttcgc cagctggcgt aatagcgaag     780
aggcccgcac cgatcgccct tcccaacagt tgcgcagcct gaatggcgaa tggcgcctga     840
tgcggtattt tctccttacg catctgtgcg gtatttcaca ccgcatatgg tgcactctca     900
gtacaatctg ctctgatgcc gcatagttaa gccagccccg acacccgcca cacccgctg     960
acgcgccctg acgggcttgt ctgctcccgg catccgctta cagacaagct gtgaccgtct    1020
ccgggagctg catgtgtcag aggttttcac cgtcatcacc gaaacgcgcg agacgaaagg    1080
gcctcgtgat acgcctattt ttataggtta atgtcatgat aataatggtt cttagacgt     1140
caggtggcac ttttcgggga atgtgcgcg gaaccctat ttgtttattt ttctaaatac      1200
attcaaatat gtatccgctc atgagacaat aaccctgata atgcttcaa taatattgaa     1260
aaaggaagag tatgagtatt caacatttcc gtgtcgccct tattccctt tttgcggcat     1320
tttgccttcc tgttttgct cacccagaaa cgctggtgaa agtaaaagat gctgaagatc     1380
agttgggtgc acgagtgggt tacatcgaac tggatctcaa cagcggtaag atccttgaga    1440
gttttcgccc cgaagaacgt tttccaatga tgagcacttt taaagttctg ctatgtggcg    1500
cggtattatc ccgtattgac gccgggcaag agcaactcgg tcgccgcata cactattctc    1560
agaatgactt ggttgagtac tcaccagtca cagaaaagca tcttacggat ggcatgacag    1620
taagagaatt atgcagtgct gccataacca tgagtgataa cactgcggcc aacttacttc    1680
tgacaacgat cggaggaccg aaggagctaa ccgcttttt gcacaacatg ggggatcatg     1740
taactcgcct tgatcgttgg gaaccggagc tgaatgaagc cataccaaac gacgagcgtg    1800
acaccacgat gcctgtagca atggcaacaa cgttgcgcaa actattaact ggcgaactac    1860
ttactctagc ttcccggcaa caattaatag actggatgga ggcggataaa gttgcaggac    1920
cacttctgcg ctcggccctt ccggctggct ggtttattgc tgataaatct ggagccggtg    1980
agcgtgggtc tcgcggtatc attgcagcac tggggccaga tggtaagccc tcccgtatcg    2040
tagttatcta cacgacgggg agtcaggcaa ctatggatga acgaaataga cagatcgctg    2100
agataggtgc ctcactgatt aagcattggt aactgtcaga ccaagtttac tcatatatac    2160
tttagattga tttaaaactt cattttaat ttaaaggat ctaggtgaag atccttttg       2220
ataatctcat gaccaaaatc ccttaacgtg agttttcgtt ccactgagcg tcagaccccg    2280
tagaaaagat caaaggatct tcttgagatc ctttttttct gcgcgtaatc tgctgcttgc    2340
```

-continued

```
aaacaaaaaa accaccgcta ccagcggtgg tttgtttgcc ggatcaagag ctaccaactc    2400
tttttccgaa ggtaactggc ttcagcagag cgcagatacc aaatactgtc cttctagtgt    2460
agccgtagtt aggccaccac ttcaagaact ctgtagcacc gcctacatac ctcgctctgc    2520
taatcctgtt accagtggct gctgccagtg gcgataagtc gtgtcttacc gggttggact    2580
caagacgata gttaccggat aaggcgcagc ggtcgggctg aacggggggt tcgtgcacac    2640
agcccagctt ggagcgaacg acctacaccg aactgagata cctacagcgt gagctatgag    2700
aaagcgccac gcttcccgaa gggagaaagg cggacaggta tccggtaagc ggcagggtcg    2760
gaacaggaga gcgcacgagg gagcttccag ggggaaacgc ctggtatctt tatagtcctg    2820
tcgggtttcg ccacctctga cttgagcgtc gatttttgtg atgctcgtca gggggcgga    2880 gcctatggaa aaacgccagc aacgcggcct ttttacggtt cctggccttt tgctggcctt    2940
ttgctcacat gttctttcct gcgttatccc ctgattctgt ggataaccgt attaccgcct    3000
ttgagtgagc tgataccgct cgccgcagcc gaacgaccga gcgcagcgag tcagtgagcg    3060
aggaagcgga agagcgccca atacgcaaac cgcctctccc cgcgcgttgg ccgattcatt    3120
aatgcagctg gcacgacagg tttcccgact ggaaagcggg cagtgagcgc aacgcaatta    3180
atgtgagtta gctcactcat taggcacccc aggctttaca ctttatgctt ccggctcgta    3240
tgttgtgtgg aattgtgagc ggataacaat ttcacacagg aaacagctat gaccatgatt    3300
acgaattcg                                                            3309

<210> SEQ ID NO 8
<211> LENGTH: 6347
<212> TYPE: DNA
<213> ORGANISM: Artificial Sequence
<220> FEATURE:
<223> OTHER INFORMATION: pMSG vector sequence
<220> FEATURE:
<221> NAME/KEY: promoter
<222> LOCATION: (1)..(419)
<220> FEATURE:
<221> NAME/KEY: terminator
<222> LOCATION: (449)..(656)
<220> FEATURE:
<221> NAME/KEY: gene
<222> LOCATION: (3365)..(6329)
<223> OTHER INFORMATION: Human beta globin MAR element
<220> FEATURE:
<221> NAME/KEY: gene
<222> LOCATION: (1272)..(2132)
<223> OTHER INFORMATION: beta-galactosidase

<400> SEQUENCE: 8
gcgcagcacc atggcctgaa ataacctctg aaagaggaac ttggttaggt accttctgag      60
gcggaaagaa ccagctgtgg aatgtgtgtc agttaggggtg tggaaagtcc ccaggctccc    120
cagcaggcag aagtatgcaa agcatgcatc tcaattagtc agcaaccagg tgtggaaagt    180
ccccaggctc cccagcaggc agaagtatgc aaagcatgca tctcaattag tcagcaacca    240
tagtcccgcc cctaactccg cccatcccgc cctaactccg cccagttccg cccattctc    300 cgccccatgg ctgactaatt tttttatttt atgcagaggc cgaggccgcc tcggcctctg    360
agctattcca gaagtagtga ggaggctttt ttggaggcct aggcttttgc aaaaagcttg    420
ctagcggccg cagatctgtt aactcgagaa cttgtttatt gcagcttata atggttacaa    480
ataaagcaat agcatcacaa atttcacaaa taaagcattt ttttcactgc attctagttg    540
tggtttgtcc aaactcatca atgtatctta tcatgtctgg atccaggata atatatggta    600
gggttcatag ccagagtaac cttttttttt aatttttatt ttatttatt tttgagctgc     660
```

```
aggcatgcaa gctggcactg gccgtcgttt tacaacgtcg tgactgggaa aaccctggcg    720
ttacccaact taatcgcctt gcagcacatc ccccttttcgc cagctggcgt aatagcgaag   780
aggcccgcac cgatcgccct tcccaacagt tgcgcagcct gaatggcgaa tggcgcctga   840
tgcggtattt tctccttacg catctgtgcg gtatttcaca ccgcatatgg tgcactctca   900
gtacaatctg ctctgatgcc gcatagttaa gccagcccg acaccgcca cacccgctg    960
acgcgccctg acgggcttgt ctgctcccgg catccgctta cagacaagct gtgaccgtct  1020
ccgggagctg catgtgtcag aggttttcac cgtcatcacc gaaacgcgcg agacgaaagg  1080
gcctcgtgat acgcctattt ttataggtta atgtcatgat aataatggtt tcttagacgt  1140
caggtggcac ttttcgggga atgtgcgcg gaaccctat ttgttattt ttctaaatac    1200
attcaaatat gtatccgctc atgagacaat aaccctgata aatgcttcaa taatattgaa  1260
aaaggaagag tatgagtatt caacatttcc gtgtcgccct tattccctt tttgcggcat   1320
tttgccttcc tgttttgct cacccagaaa cgctggtgaa agtaaaagat gctgaagatc    1380
agttgggtgc acgagtgggt tacatcgaac tggatctcaa cagcggtaag atccttgaga  1440
gttttcgccc cgaagaacgt tttccaatga tgagcacttt taaagttctg ctatgtggcg  1500
cggtattatc ccgtattgac gccgggcaag agcaactcgg tcgccgcata cactattctc  1560
agaatgactt ggttgagtac tcaccagtca cagaaaagca tcttacggat ggcatgacag  1620
taagagaatt atgcagtgct gccataacca tgagtgataa cactgcggcc aacttacttc  1680
tgacaacgat cggaggaccg aaggagctaa ccgcttttt gcacaacatg ggggatcatg    1740
taactcgcct tgatcgttgg gaaccggagc tgaatgaagc cataccaaac gacgagcgtg  1800
acaccacgat gcctgtagca atggcaacaa cgttgcgcaa actattaact ggcgaactac   1860
ttactctagc ttcccggcaa caattaatag actggatgga ggcggataaa gttgcaggac  1920
cacttctgcg ctcggccctt ccggctggct ggtttattgc tgataaatct ggagccggtg  1980
agcgtgggtc tcgcggtatc attgcagcac tggggccaga tggtaagccc tcccgtatcg  2040
tagttatcta cacgacgggg agtcaggcaa ctatggatga acgaaataga cagatcgctg  2100
agataggtgc ctcactgatt aagcattggt aactgtcaga ccaagtttac tcatatatac  2160
tttagattga tttaaaactt catttttaat ttaaaaggat ctaggtgaag atcctttttg  2220
ataatctcat gaccaaaatc ccttaacgtg agttttcgtt ccactgagcg tcagaccccg  2280
tagaaaagat caaaggatct tcttgagatc ctttttttct gcgcgtaatc tgctgcttgc  2340
aaacaaaaaa accaccgcta ccagcggtgg tttgtttgcc ggatcaagag ctaccaactc  2400
tttttccgaa ggtaactggc ttcagcagag cgcagatacc aaatactgtc cttctagtgt  2460
agccgtagtt aggccaccac ttcaagaact ctgtagcacc gcctacatac ctcgctctgc  2520
taatcctgtt accagtggct gctgccagtg gcgataagtc gtgtcttacc gggttggact  2580
caagacgata gttaccggat aaggcgcagc ggtcgggctg aacggggggt tcgtgcacac  2640
agcccagctt ggagcgaacg acctacaccg aactgagata cctacagcgt gagctatgag  2700
aaagcgccac gcttcccgaa gggagaaagg cggacaggta tccggtaagc ggcagggtcg  2760
gaacaggaga gcgcacgagg gagcttccag ggggaaacgc ctggtatctt tatagtcctg  2820
tcgggtttcg ccacctctga cttgagcgtc gatttttgtg atgctcgtca gggggggcgga  2880
gcctatggaa aaacgccagc aacgcggcct ttttacggtt cctggccttt tgctggcctt  2940
ttgctcacat gttctttcct gcgttatccc ctgattctgt ggataaccgt attaccgcct  3000
```

```
ttgagtgagc tgataccgct cgccgcagcc gaacgaccga gcgcagcgag tcagtgagcg    3060
aggaagcgga agagcgccca atacgcaaac cgcctctccc cgcgcgttgg ccgattcatt    3120
aatgcagctg gcacgacagg tttcccgact ggaaagcggg cagtgagcgc aacgcaatta    3180
atgtgagtta gctcactcat taggcacccc aggctttaca ctttatgctt ccggctcgta    3240
tgttgtgtgg aattgtgagc ggataacaat ttcacacagg aaacagctat gaccatgatt    3300
acgccaagct cgaaattaac cctcactaaa gggaacaaaa gctggagctc caccgcggcc    3360
cgggcctcct gagtagctgg gactacaggt gtacatcaca tgcctggcta atttttttt    3420 tttaagtaga gacgaggtct tgctatgttg tccaggataa tatcaaactc ttgagctcaa    3480
gcagtcctcc cacttctacc tctcaagtgc tggaattaca gacatgagcc accactcctg    3540
gcttgcagac tatttaaatg actaattcct gacactgctt gagggatact agacagtaga    3600
caacacatct ttaatatacc aaatgggtga ctgtagggtt gagagggaga ttagaattca    3660
atgttttatg accaaaaagg cttaaatcag gcacaagctt aggtcttttc aactgtgagg    3720
accggactga aagtgtgcag ttcaaggccc tgtagttgct gtttaactgt tcccaggtgg    3780
aagtctcttc aaagaaccac tggtgcaaaa agggaactac ctggggataa atatttcctc    3840
cagaaagggg gaaagtgcaa gctcccctac caaaagcacc aggcaagtcc ttgtctattt    3900
tccctgaagt tctcaaagaa atgagaccct tgtttacctt taagattaga gaaggcttga    3960
aaagtttgag ctgtgccttt ggaggccaac aaactttttct cctttgttga ccaagttcag    4020
ctctcctgta tacttccaag gtctgttgca tcaagagtga gaattgaagg tcttagaagc    4080
tgggatctca gatgtaggga aaagaggaga tttcctgttc actcactgtt aagatatggc    4140
tgaaattttt tgatctagtc atctacaaag catgagttgt gggtcagaaa ttgtttttca    4200
catcttttga cttcctttga catcagaata taacctagga attgattact taagtgaagg    4260
caaggtactt tggtctggac aggaacattt tgaacaaggt agggagacag ctatgaaggc    4320
aagcatttat tctatctatc atctatctgt ctatctatct attctttcat ccacttattt    4380
atacatttaa acaaaaagta tagagcgtag tataatttgt aagtgctcag gctgtgtgt    4440 gtatggattg tttgaaatga aactaaagtg ggagtataat tctactgccc ccttaacccct    4500 gtggtcccta cactaccctg caagactctt agctgcttag cttaattgtg aggctgatt    4560 ggggcatagc acccatcctc tctgtctttc aacatcctca taataacttg agataatttt    4620
ataaaatatc acaataggt catgttcagt agggtgatat ataaaattag acaagccata    4680
gtttgagtta ccctttgaa taaatatatg acaaaaggca atttaattat ctttatgagt    4740
ttggaggtat ccagtatgaa atttagataa tacctgcctt ctagtgttga aattagaact    4800
taatgatata atgcatcaat gaacttatta tagttcctag cacaaagtaa gaatcctttc    4860
aatgtgtgtg tgtgtgtatg tatttatctg ttattaatag gaatcttata gggcattatc    4920
tcacttaatc cttattaata actatgaagc aggtatttat ttgagttttc caagtgagtt    4980
aagtatagct tgtaatactt aaggaaatat ccacaggtta catagctagt ataactga    5040 gaaataattt tatttatatt ataaaacatt ctaacaatac agatgtatat aaactaaaaa    5100
actgaaaggg ctcatgcaac cctaccttct caatatcact tcttcactta gaaaaaacca    5160
gccttagctg tctgctatga atcctttcaa aatatacttc tgagaaatga gagagagaaa    5220
tggggagggt agaaggaagg aagatagggt aagagacagg gaaggaggtg tggggaaaga    5280
aattaaatta ttcttttctc tgtctcttga aagagctctt tccattacat tgaatcaaag    5340
gtaatgttgc catttctgga ctcttgaaat aaagaaagac cgatgtatga aataatttg    5400
```

```
aaagtctatg gcattttcaa aatgcaaggt gatgtcttac taactagcct ttgctttatt    5460
attagaaatg gggaagtgag tatagacatt ttatcaggag atatattagg aaaaagggaa    5520
actggagaaa ctgggaggag tatccagatg tcctgtccct gtaaggtggg ggcacccacc    5580
ttcaatcaaa agggctcctt aacaacttcc ttgcttgggg ctccaccatc ttggaccatt    5640
agctccacag gtatcttctt ccctctagtg gtcataacag cagcttcagc tacctctcta    5700
aagagtcctg ccagatatag gtcaggaaat ataaccacta ataaaagag aaacattttg     5760 actgtagttg tttgttttt gtcattgtga ctatcaataa cattctcact ctttcatcag     5820
taatcactca ggttattctg tgaccaacag actgtgggaa aaatcagaga aggaggcatc    5880
ctcatgctta ctagcctaaa ctgaaattgc tatagcagag tgaaccagaa ggtttacaga    5940
tattttccac aaagagtaaa aggattgaag ccttctccag atcaatgcat aggaaataat    6000
aatggaccat aaaacccata ttatgacgaa caacattagg ataagtccat atcaattttt    6060
aatccagtca taagcacaga ctacgtgaag cacgtccaag tgaaggcagg agaaatgaga    6120
ggagcaagaa agaggagcca tttgatcaag aatagcagaa aaggaaagg caagtcatat     6180 taacaaatga ttgtcatgcc aacagtacag ataactctgc taataaaggt agaggcataa    6240
tacaggtagt agcagatatc tacatagtag ttaaaggaca tggccatcag tacagaagat    6300
tccataaagg agaacctaaa gaggaagaaa tcgataagct tgatccc                  6347
```

<210> SEQ ID NO 9
<211> LENGTH: 20
<212> TYPE: DNA
<213> ORGANISM: Artificial Sequence
<220> FEATURE:
<223> OTHER INFORMATION: BML1 primer for human beta globin nuclear
      matrix attachment region element
<220> FEATURE:
<221> NAME/KEY: primer
<222> LOCATION: (1)..(20)

<400> SEQUENCE: 9
ttcttcctct ttaggttctc                                                 M20

<210> SEQ ID NO 10
<211> LENGTH: 20
<212> TYPE: DNA
<213> ORGANISM: Artificial Sequence
<220> FEATURE:
<223> OTHER INFORMATION: BMR1 primer for human beta globin nuclear
      matrix attachment region element
<220> FEATURE:
<221> NAME/KEY: primer
<222> LOCATION: (1)..(20)
<223> OTHER INFORMATION: primer

<400> SEQUENCE: 10
cctcctgagt agctgggact                                                 20

<210> SEQ ID NO 11
<211> LENGTH: 41
<212> TYPE: DNA
<213> ORGANISM: Artificial Sequence
<220> FEATURE:
<223> OTHER INFORMATION: CMVL1 primer for pcCNA3.1 vector
<220> FEATURE:
<221> NAME/KEY: primer_
<222> LOCATION: (1)..(41)
<223> OTHER INFORMATION: primer

<400> SEQUENCE: 11

-continued attccgcgga tcgattcgcg atgtacgggc cagatatacg c        41

<210> SEQ ID NO 12
<211> LENGTH: 23
<212> TYPE: DNA
<213> ORGANISM: Artificial Sequence
<220> FEATURE:
<223> OTHER INFORMATION: PAR1 primer for pcCDNA3.1 vector
<220> FEATURE:
<221> NAME/KEY: primer
<222> LOCATION: (1)..(23)
<223> OTHER INFORMATION: primer

<400> SEQUENCE: 12
attgaatgca gtgaaaaaaa tgc        23

<210> SEQ ID NO 13
<211> LENGTH: 39
<212> TYPE: DNA
<213> ORGANISM: Artificial Sequence
<220> FEATURE:
<223> OTHER INFORMATION: PKL1 primer for scu-PA gene
<220> FEATURE:
<221> NAME/KEY: primer
<222> LOCATION: (1)..(39)
<223> OTHER INFORMATION: primer

<400> SEQUENCE: 13
cccaagctta tgagagccct gctggcgcgc ctgcttctc        39

<210> SEQ ID NO 14
<211> LENGTH: 27
<212> TYPE: DNA
<213> ORGANISM: Artificial Sequence
<220> FEATURE:
<223> OTHER INFORMATION: PKR1 primer of asc-PA gene
<220> FEATURE:
<221> NAME/KEY: primer_
<222> LOCATION: (1)..(27)
<223> OTHER INFORMATION: primer

<400> SEQUENCE: 14
tcccccgggt cagagggcca ggccatt        27

<210> SEQ ID NO 15
<211> LENGTH: 87
<212> TYPE: DNA
<213> ORGANISM: Artificial Sequence
<220> FEATURE:
<223> OTHER INFORMATION: sense sequence of gastrin termination site used
      in pSG vector
<220> FEATURE:
<221> NAME/KEY: terminator
<222> LOCATION: (1)..(87)
<223> OTHER INFORMATION: sense sequence of gastrin termination site

<400> SEQUENCE: 15
agcggatcca ggataatata tggtagggtt catagccaga gtaaccttt tttttaattt        60 ttatttttatt ttattttga gctgcag        87

<210> SEQ ID NO 16
<211> LENGTH: 87
<212> TYPE: DNA
<213> ORGANISM: Artificial Sequence
<220> FEATURE:
<223> OTHER INFORMATION: antisense sequence of gastrin germination site
      used in pSG vector
<220> FEATURE:

```
<221> NAME/KEY: terminator
<222> LOCATION: (1)..(87)
<223> OTHER INFORMATION: antisense sequence of gastrin termination site

<400> SEQUENCE: 16
ctgcagctca aaataaaat aaaataaaaa ttaaaaaaaa aggttactct ggctatgaac      60
cctaccatat attatcctgg atccgct                                        87

<210> SEQ ID NO 17
<211> LENGTH: 35
<212> TYPE: DNA
<213> ORGANISM: Artificial Sequence
<220> FEATURE:
<223> OTHER INFORMATION: ML1 primer for amplyfing human beta globin MAR
      element in pMS vector
<220> FEATURE:
<221> NAME/KEY: primer
<222> LOCATION: (1)..(35)
<223> OTHER INFORMATION: primer

<400> SEQUENCE: 17
tccccgcggc ccgggcctcc tgagtagctg ggact                               35

<210> SEQ ID NO 18
<211> LENGTH: 35
<212> TYPE: DNA
<213> ORGANISM: Artificial Sequence
<220> FEATURE:
<223> OTHER INFORMATION: MR1 primer for amplyfing human beta globin MAR
      element in pMS vector
<220> FEATURE:
<221> NAME/KEY: primer
<222> LOCATION: (1)..(35)
<223> OTHER INFORMATION: primer

<400> SEQUENCE: 18
ttggggccca tcgatttctt cctctttagg ttctc                               35

<210> SEQ ID NO 19
<211> LENGTH: 39
<212> TYPE: DNA
<213> ORGANISM: Artificial Sequence
<220> FEATURE:
<223> OTHER INFORMATION: TL1 primer of gastrin termination site
      in pSG vector
<220> FEATURE:
<221> NAME/KEY: primer
<222> LOCATION: (1)..(39)
<223> OTHER INFORMATION: primer

<400> SEQUENCE: 19
gaagatctgt taactcgaga acttgtttat tgcagctta                           39

<210> SEQ ID NO 20
<211> LENGTH: 20
<212> TYPE: DNA
<213> ORGANISM: Artificial Sequence
<220> FEATURE:
<223> OTHER INFORMATION: TR1 primer of gastrin termnation site
      in pSG vector
<220> FEATURE:
<221> NAME/KEY: primer
<222> LOCATION: (1)..(20)
<223> OTHER INFORMATION: primer

<400> SEQUENCE: 20
gtgccagctt gcatgcctgc                                                20
```

<210> SEQ ID NO 21
<211> LENGTH: 34
<212> TYPE: DNA
<213> ORGANISM: Artificial Sequence
<220> FEATURE:
<223> OTHER INFORMATION: PL1 primer for fusing SV40 virus promoter and multicloning site
<220> FEATURE:
<221> NAME/KEY: primer
<222> LOCATION: (1)..(34)
<223> OTHER INFORMATION: primer

<400> SEQUENCE: 21
ccatcgatgg gcccgcgcag caccatggcc tgaa                                  34

<210> SEQ ID NO 22
<211> LENGTH: 40
<212> TYPE: DNA
<213> ORGANISM: Artificial Sequence
<220> FEATURE:
<223> OTHER INFORMATION: PR1 primer for fusing SV40 virus promoter and multicloning site
<220> FEATURE:
<221> NAME/KEY: primer
<222> LOCATION: (1)..(40)
<223> OTHER INFORMATION: primer

<400> SEQUENCE: 22
gaagatctgc ggccgctagc aagcttttttg caaaagccta                           40

<210> SEQ ID NO 23
<211> LENGTH: 29
<212> TYPE: DNA
<213> ORGANISM: Artificial Sequence
<220> FEATURE:
<223> OTHER INFORMATION: TRI primer of TGF-beta soluble receptorII
<220> FEATURE:
<221> NAME/KEY: primer
<222> LOCATION: (1)..(29)
<223> OTHER INFORMATION: primer

<400> SEQUENCE: 23
accgctagcc cacccatggg tcggggct                                         29

<210> SEQ ID NO 24
<211> LENGTH: 29
<212> TYPE: DNA
<213> ORGANISM: Artificial Sequence
<220> FEATURE:
<223> OTHER INFORMATION: TRRI primer of TGF soluble receptor II
<220> FEATURE:
<221> NAME/KEY: primer
<222> LOCATION: (1)..(29)
<223> OTHER INFORMATION: primer

<400> SEQUENCE: 24
agcctcgagc tagtcaggat tgctggtgt                                        29